(12) United States Patent
de Prisco et al.

(10) Patent No.: US 9,183,326 B2
(45) Date of Patent: Nov. 10, 2015

(54) METHOD FOR SIMULATING FRACTIONAL MULTI-PHASE/MULTI-COMPONENT FLOW THROUGH POROUS MEDIA

(75) Inventors: Giuseppe de Prisco, Houston, TX (US); Jonas Toelke, Houston, TX (US); Yaoming Mu, Houston, TX (US)

(73) Assignee: Ingrain, Inc., Houston, TX (US)

( * ) Notice: Subject to any disclaimer, the term of this patent is extended or adjusted under 35 U.S.C. 154(b) by 559 days.

(21) Appl. No.: 13/539,543

(22) Filed: Jul. 2, 2012

(65) Prior Publication Data

US 2013/0018641 A1    Jan. 17, 2013

Related U.S. Application Data

(60) Provisional application No. 61/506,680, filed on Jul. 12, 2011.

(51) Int. Cl.
  *G06G 7/57* (2006.01)
  *G01N 15/08* (2006.01)
  *G06F 17/50* (2006.01)

(52) U.S. Cl.
  CPC ........ *G06F 17/5009* (2013.01); *G06F 2217/16* (2013.01)

(58) Field of Classification Search
  CPC .................................. G06G 7/57; G01N 15/08
  See application file for complete search history.

(56) References Cited

U.S. PATENT DOCUMENTS

| | | | |
|---|---|---|---|
| 2,345,935 A | 4/1944 | Hassler | |
| 4,506,542 A | 3/1985 | Rose | |
| 5,497,321 A | 3/1996 | Ramakrishnan et al. | |
| 6,021,662 A | 2/2000 | Moulu et al. | |
| 6,516,080 B1 | 2/2003 | Nur | |
| 2003/0060988 A1* | 3/2003 | Ginzburg | 702/50 |
| 2007/0276639 A1* | 11/2007 | Montaron et al. | 703/10 |
| 2010/0128932 A1 | 5/2010 | Dvorkin et al. | |
| 2010/0135536 A1 | 6/2010 | Dvorkin et al. | |

OTHER PUBLICATIONS

B. Ahrenholz et al., "Prediction of capillary hysteresis in a porous material using lattice-Boltzmann methods and comparison to experimental data and a morphological pore network model," Advances in Water Resources, vol. 31, Issue 9, Sep. 2008, pp. 1151-1173.*

(Continued)

*Primary Examiner* — Omar Fernandez Rivas
*Assistant Examiner* — Bijan Mapar
(74) *Attorney, Agent, or Firm* — Kilyk & Bowersox, P.L.L.C.

(57) ABSTRACT

A method for computing or estimating fractional, multi-phase/multi-component flow through a porous medium employing a 3D digital representation of a porous medium and a computational fluid dynamics method to calculate flow rates, pressures, saturations, internal velocity vectors and other flow parameters is described. The method employs a unique method of introducing non-wetting and wetting fluids into the pores at the inlet face of the 3D digital representation of a porous medium and a novel process control application to achieve quasi-steady state flow at low inlet concentrations of non-wetting fluid. In addition, the method of the present invention reduces the time required to simulate to complete the fluid dynamic calculations. The resulting values of flow of non-wetting fluid, wetting fluid, saturation, and other parameters are used to generate plots of relative permeability imbibition and drainage curves. Computerized systems and programs for performing the method are also provided.

48 Claims, 10 Drawing Sheets

(56) References Cited

OTHER PUBLICATIONS

U. Frisch et al., "Lattice Gas Hydrodynamics in Two and Three Dimensions," Complex Systems, 1987, pp. 649-707.*
A.J. Wagner, "A Practical Introduction to the Lattice Boltzmann Method," Dept. of Physics, North Dakota State University, Fargo, Mar. 2008.*
J. Tölke et al., "Computer simulations of fluid flow in sediment: From Images to permeability," Special Section: High-Performance Computing, The Leading Edge, Jan. 2010, pp. 68-74.*
M.L. Porter et al., "Lattice-Boltzmann simulations of the capillary pressure-saturation-interfacial area relationship for porous media," Advances in Water Resources, 32 (2009), pp. 1632-1640.*
P. Iassonov et al., "Segmentation of X-ray computed tomography images of porous materials: A crucial step for characterization and quantitative analysis of pore structures," Water Resources Research, vol. 45, W09415, 2009.*
B. Ahrenholz et al., "Pore-scale determination of parameters for macroscale modeling of evaporation processes in porous media," Water Resources Research, vol. 47, W07543, 2011.*
Rose, W., "Some Problems in Applying the Hassler Relative Permeability Method," 32 J. Petroleum Techology, 1161-63 (Jul. 1980).
Gunstensen et al., "Lattice-Boltzmann Studies of Immiscible Two-Phase Flow Through Porous Media," J. of Geophysical Research, vol. 98, No. B4, Apr. 10, 1993, pp. 6431-6441.
Naar, J. et al., "Three-Phase Imbibition Relative Permeability," Soc. Pet. Eng. J., 12, 254-258, 1961.
Saraf, D.N. et al., "Three-Phase Relative Permeability Measurement Using a Nuclear Magnetic Resonance Technique for Estimating Fluid Saturation," Soc. Pet. Eng. J., 9, 235, 1967.
Ladd, A. J. C., "Numerical Simulations of Particulate Suspensions Via a Discretized Boltzmann Equation," Part 1: Theoretical Foundation, J. Fluid Mech., vol. 271, 1994, pp. 285-309.
Gunstensen et al., "Lattice-Boltzmann Model of Immiscible Fluids," Phys. Rev. A., vol. 43, No. 8, Apr. 15, 1991, pp. 4320-4327.
Olson, J. F., et al., "Two-Fluid Flow in Sedimentary Rock: Simulation, Transport and Complexity," J. Fluid Mechanics, vol. 341, 1997, pp. 343-370.
Grader, Avrami et al., "Estimation of Relative Permeability using the Lattice Boltzmann Method for Fluid Flows in a Cretaceous Formation, Abu Dhabi," Society of Petroleum Engineers, Nov. 1, 2010-Nov. 4, 2010, SPE138591, pp. 1-8.
Ramstad, Thomas et al., "Simulation of Two Phase Flow in Reservoir Rocks Using a Lattice Boltzmann Method," Society of Petroleum Engineers, Oct. 4, 2009-Oct. 7, 2009, SPE124617, pp. 1-16.
Rivas-Gomez, S. et al., "Numerical Simulation of Oil Displacement by Water in a Vuggy Fractured Porous Medium," Society of Petroleum Engineers, Feb. 11, 2001-Feb. 14, 2001, SPE 66386, pp. 1-9.
Annex to Form PCT/ISA/206, Communication Relating to the Results of the Partial International Search, dated May 17, 2013, received in corresponding International Patent Application No. PCT/US2012/045220.
International Search Report and Written Opinion issued in corresponding International Patent Application No. PCT/US2012/045220, dated Sep. 9, 2013 (17 pages).

* cited by examiner

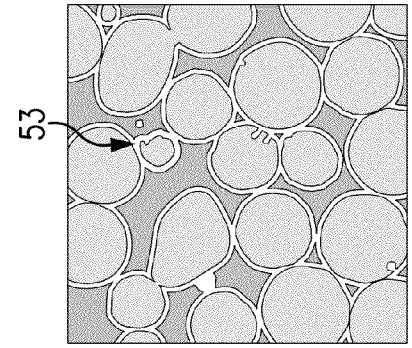
FIG. 5c
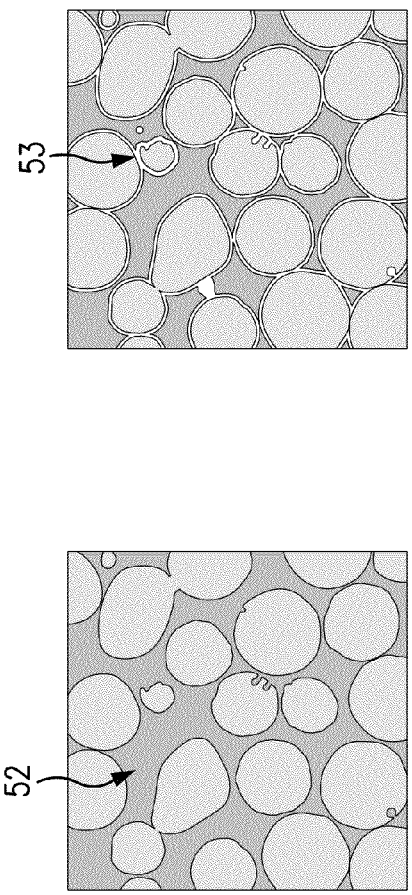
FIG. 5b
FIG. 5a
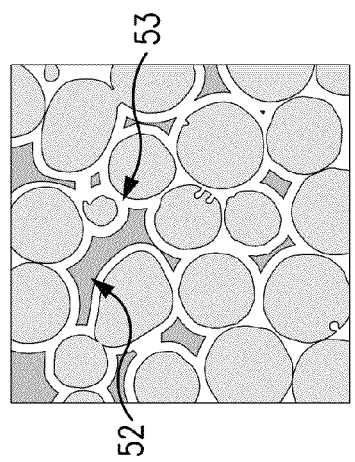
FIG. 5f
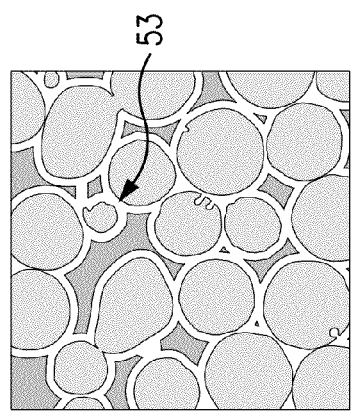
FIG. 5e
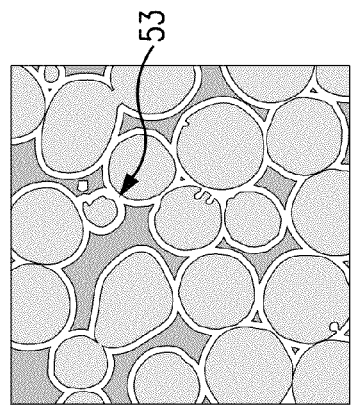
FIG. 5d

METHOD FOR SIMULATING FRACTIONAL MULTI-PHASE/MULTI-COMPONENT FLOW THROUGH POROUS MEDIA

This application claims the benefit under 35 U.S.C. §119 (e) of prior U.S. Provisional Patent Application No. 61/506,680, filed Jul. 12, 2011, which is incorporated in its entirety by reference herein.

BACKGROUND OF THE INVENTION

The present invention relates to a method to estimate multiphase/multi-component fluid flow through porous media and to estimate relative permeabilities at various levels of saturation. Relative permeability data estimated with the present method can be used, for example, in many areas such as oil field simulation, estimating oil or gas production rates, estimating recoverable reserves, designing hydrocarbon recovery strategies such as fracturing or "fracking", life sciences, paper manufacturing, food industry, agriculture, and other areas relating to geology and geophysics. The present invention also relates to a computerized system and components thereof for performing such a method.

Relative permeability is used to quantify multiphase flow, such as the flow of oil in the presence of water and water in the presence of oil. In a sample with two such fluids, the relative permeabilities $k_{rn}$ and $k_{rw}$, by definition, are given by equations [9] and [10]:

$$k_{rn} = -\frac{Q_n \mu_n}{k_{Absolute} A \, dp/dx} \quad [9]$$

$$k_{rw} = -\frac{Q_w \mu_w}{k_{Absolute} A \, dp/dx} \quad [10]$$

where the subscripts "n" and "w" refer to non-wetting fluid and wetting fluid, respectively. The fluxes $Q_n$ and $Q_w$ are measured at fixed saturation $S_w$. Relative permeability is usually plotted versus $S_w$.

The relative permeability depends on more factors than $k_{Absolute}$, including the wettability of the fluids and minerals system, interfacial surface tension, and viscosity contrast between the fluid phases, the velocities of the fluids, the saturation level of the fluid in the pores, the structure and connectivity of the pores in the porous solid and the pore space geometry. Another important factor that influences the relative permeability is the time history of the flows that went through the porous media. These parameters may vary in space and time and the resulting fluid state and composition changes during production of fluids.

In a porous medium, capillary attraction is determined by the adhesion between a liquid present in the body and the body itself and by the cohesive force of the liquid to itself. A liquid that wets a solid surface has greater adhesion to the particular solid than a non-wetting fluid. A fluid may wet one solid and not another solid. In multiphase fluid flow, wettability is a relative property. For example, if the force of adhesion of a first fluid for a porous medium is greater than the force of adhesion of a second fluid for a porous medium, then the first fluid is said to be wetting and the second fluid is said to be non-wetting.

Saturation, $S_x$, is the volume fraction of the total pore volume in a porous medium that is occupied by material "X". The saturation level is a value between 0 and 1. A saturation level of 1 indicates that the entire available pore space in a given porous medium is filled by the fluid under consideration. Relative permeabilities are a function of fluid saturation. As the saturation of a particular phase increases, its relative permeability increases. Saturation history also has a major effect on relative permeability. The relative permeability-saturation relationship exhibits a hysteresis effect between the drainage process (wetting phase decreasing) and imbibition process (non-wetting phase increasing). It is believed that most subterranean porous rock formations were initially water filled and hydrocarbons entered these porous formations displacing part of the water. This history must be reproduced or assessed before any estimation of relative permeability is attempted so that realistic starting conditions are established. Imbibition and drainage plots of relative permeability versus saturation are shown in FIG. 1.

When a porous medium contains two or more immiscible fluids, the local volume of material in any particular pore may be different from the overall or average saturation level for the entire porous rock sample. For example, one fluid may strongly adhere to the surfaces within a given pore while another material may have no effective contact with the solid material. The local pore space geometry within a given porous medium can vary considerably and these variations in geometry can effect local saturation levels.

In practice, relative permeability can be estimated by physical lab tests or by numerical simulations.

One of the early physical lab methods for measuring relative permeability is described in U.S. Pat. No. 2,345,935 (Hassler). The method involves sealing all but two opposing surfaces on a porous rock sample. A fluid or fluids under pressure are introduced into one open surface and forced to flow through the sample at a specified flow rate. Fluid pressures are generated by pumps or similar means. The pressures and flux rates are inputs to the relative permeability calculation. One shortcoming of the Hassler technique is the need to determine internal wetting fluid pressures within the porous medium. This problem is described by W. Rose, "Some Problems in Applying the Hassler Relative Permeability Method," 32 J. Petroleum Technology, 1161-63 (July, 1980). U.S. Pat. No. 4,506,542 (Rose) describes an apparatus and method that does not require measurement of internal pressures for estimation of relative permeability.

The Hassler method is a Steady State Method that can be used to calculate relative permeability versus saturation for a full range of saturations from 0 to 1. For two phase systems of immiscible fluids, the rock sample may first be purged with one fluid for a sufficient time such that the saturation in the rock sample of the selected fluid is 1. Then the other fluid or combinations of the two fluids are forced through the sample for a sufficient time to achieve steady state of the two fluxes $Q_n$ and $Q_w$. At this point, the flux and pressure readings can be used to calculate $k_n$, $k_w$ for a given value of $S_w$ and plotted. The ratio of wetting and non-wetting fluids at the inlet of the sample can then be changed. This new combination of wetting and non-wetting fluids are forced through the sample for a sufficient time to achieve steady state of the two fluxes $Q_n$ and $Q_w$. Another pair of relative permeabilities, $k_n$, $k_w$ corresponding to another value of $S_w$, are calculated and another point is plotted. By repeating this procedure for different combinations of wetting and non-wetting fluids, a graph of relative permeability versus saturation can be plotted as shown in FIG. 2.

Other steady state physical methods to compute relative permeability include the Penn State Method (Snell, R. W., Measurements of gas-phase saturation in a porous medium, J. Inst. Pet., 45 (428), 80, 1959; The Hafford method (Naar, J. et al., Three-phase imbibition relative permeability, Soc. Pet. Eng. J., 12, 254, 1961); the Single-Sample Dynamic Method (Saraf, D. N. et al., Three-phase relative permeability measurement using a nuclear magnetic resonance technique for estimating fluid saturations, Soc. Pet. Eng. J., 9, 235, 1967); the Stationary Fluid Method (Saraf, D. N. et al., Three-phase relative permeability measurement using a nuclear magnetic resonance technique for estimating fluid saturations, Soc. Pet. Eng. J., 9, 235, 1967); and the Dispersed Feed Method (Saraf, D. N. et al., Three-phase relative permeability measurement using a nuclear magnetic resonance technique for estimating fluid saturations, Soc. Pet. Eng. J., 9, 235, 1967).

Another method, the Un-Steady State Method, also begins with the rock sample initially saturated with the wetting fluid. Then the non-wetting fluid is forced through the sample, the fraction of non-wetting fluid recovered and the pressure drop across the sample are recorded and used to calculate various combinations of $k_n$, $k_w$ at corresponding values of $S_w$.

Laboratory methods can suffer from a number of shortcomings, which may include one or more the following:
1. The sample to be tested is in the lab at surface conditions whereas the in-situ sample may be at temperatures above 100° C. and 100-700 bar. When samples are brought to the surface many properties of the rock change. Creating artificial conditions to replicate downhole conditions is difficult, expensive, and/or imprecise.
2. The pressures required to achieve desired flow rates may be extremely high causing leakage problems and/or equipment malfunctions.
3. A large volume of fluid must be processed for the sample to come close to steady state.
4. Tests can take a very long time up to weeks or months or more than a year to complete.
5. Very tight formations such as shales may be difficult or impossible to measure.
6. Initial conditions such as saturation, wettability, and fluid distributions are difficult to establish.
7. Establishing wettability in the lab is difficult because cores are usually cleaned prior to the testing and initial wettability cannot be accurately restored.
8. In the lab, it is difficult and expensive to conduct tests with reservoir fluids at reservoir conditions. Mixing gas and oil at reservoir temperatures and pressures is difficult and can be dangerous.

Numerical simulations to calculate relative permeability typically use numerical methods such as pore network modeling or direct simulation of multi-phase/multi-component flow in a porous medium.

One such general method to compute relative permeability is described in U.S. Pat. No. 6,516,080 (Nur). This method as with most numerical methods relies on production of a digital representation of a porous medium, hereinafter referred to as a "Sample," for which relative permeability is to be estimated. The digital representation is typically produced by a CT X-ray scanner and then refined to compensate for limitations in resolution of the scanner. This representation along with fluid properties, rock properties, initial saturation, wettability, interfacial tension and viscosities are used as input to the lattice Boltzmann algorithm. The Lattice-Boltzmann method is a tool for flow simulation, particularly in media with complex pore geometry. See, for example, Ladd, Numerical Simulations of Particulate Suspensions via a discretized Boltzmann Equation, Part 1: Theoretical Foundation, J. Fluid Mech., v 271, 1994, pp. 285-309; Gunstensen et al., "Lattice Boltzmann Model of Immiscible Fluids, Phys. Rev. A., v. 43, no. 8, Apr. 15, 1991, pp. 4320-4327; Olsen et al., Two-fluid Flow in Sedimentary Rock: Simulation, Transport and Complexity, J. Fluid Mechanics, Vol. 341, 1997, pp. 343-370; and Gustensen et al., Lattice-Boltzmann Studies of Immiscible Two-Phase Flow Through Porous Media," J. of Geophysical Research, V. 98, No. B 4, Apr. 10, 1993, pp. 6431-6441). The Lattice-Boltzmann method simulates fluid motion as collisions of imaginary particles, which are much larger than actual fluid molecules, but wherein such particles show almost the same behavior at a macroscopic scale. The algorithm used in the Lattice-Boltzmann method repeats collisions of these imaginary particles until steady state is reached, and provides a distribution of local mass flux.

The accuracy of numerical methods to calculate relative permeability such as the Nur method depends in part on the accuracy of the Sample. The Sample is made up of discrete elements called voxels. Voxels are volumetric pixels. A digital representation of a three-dimensional object can be sub-divided into voxels. Ideally, each voxel is accurately classified as either solid or pore. The choice between solid or pore may not always be clear due to differences in the resolution of the scan and the minimum size of the grains in the porous medium. If a voxel is classified as solid, the nature or composition of the solid also should be known or determined in order to numerically model and make estimates of its physical properties.

In addition, the accuracy of numerical methods to compute relative permeability also depends on the numerical methods applied. The robustness of these methods can depend upon how boundary conditions in the algorithm are handled. There can be inlet and outlet boundary conditions, boundary conditions on the top, bottom, left or right of the sample and boundary conditions on the interior of the porous medium. The latter include effects on wettabillity especially when relatively small fractional flows of one fluid or the other are present. Boundary conditions are a quite complex problem in numerical methods. Selection of boundary conditions can significantly affect the time required for computation, the accuracy of results and the stability of the simulation. This can be especially true for immiscible multi-phase or multi-component simulations. Difficulties can arise from the fact that the pressure and distribution of the phases and velocities at the inlet of the digital simulation are unknown and these conditions must be established such that they mimic the physical conditions. There is no standardized and unique way of setting appropriate boundary conditions and many authors propose their own solution. The boundary conditions chosen can be of primary importance since they significantly can affect the numerical accuracy of the simulation and also its stability.

Numerical methods can have advantages over laboratory methods, such as in one or more of the following ways.
1. Because numerical simulations are virtual, they do not require the physical presence such as downhole fluids at downhole conditions. In the case of relative permeability in oil and gas formations, hydrocarbons at high temperatures and pressures, often above the critical point, are difficult to control and dangerous to handle.
2. Because numerical simulations can accelerate the time scale used, numerical simulations can be completed in a matter of hours or days instead of weeks, months, or longer. Because of this, more variations in fluid composition and flux can be processed using numerical methods than are practical in lab tests.
3. Numerical simulations have the advantage that the properties of any component can be accurately calculated at any location and at any time.

Numerical methods also may suffer some drawbacks, including one or more of the following:
1. Initial and boundary conditions are difficult or impossible to assess which results in inability in some cases to accurately calculate relative permeabilities or instability in computation. This is especially true when fractional flow of one or more components is small.

2. The distribution of wettability in space and time within a porous medium is difficult to assess.

The present investigators have recognized that there is a need for new methods and systems for simulating fractional multi-phase, multi-component fluid flow through porous media to provide, for example, improved evaluations and estimates of the potential productivity of an oil field or other subterranean reservoir, and/or which may provide improved modeled estimates of multi-phase, multi-component fluid flow through other types of porous media.

SUMMARY OF THE INVENTION

A feature of the present invention is a method to calculate or estimate fractional multi-phase, multi-component fluid flow through porous media.

A further feature of the present invention is a method to calculate or estimate relative permeability for fractional multi-phase, multi-component fluid flow through porous media.

Another feature of the present invention is a method to set boundary conditions for numerical methods, for instance, for computational fluid dynamics (CFD) simulations, that more accurately represent real-world conditions and improve calculation speed and stability.

Yet another feature of the present invention is a method to adjust inlet pressures for CFD calculations to achieve targeted fractional flow through a porous medium.

A further feature of the present invention is a method to calculate or estimate multiphase, multi-component fluid flow through porous media under conditions where the fraction of non-wetting or wetting fluid is low.

An additional feature of the present invention is a method to calculate or estimate relative permeability versus saturation for imbibition and drainage.

A further feature of the present invention is a method to calculate or estimate relative permeability versus saturation curves including data points where the saturation level is low.

A further feature of the present invention is a method of using the calculated or estimated relative permeabilities to evaluate a subterranean oil reservoir or other type of porous media.

To achieve these and other advantages and in accordance with the purposes of the present invention, as embodied and broadly described herein, the present invention relates, in part, to a method for simulating fractional flow of wetting fluids and non-wetting fluids through porous medium comprising the steps of (a) creating a three dimensional digital representation of a porous medium ("Sample") containing a total volume of fluids comprising wetting fluids and non-wetting fluids, (b) defining a first fraction of the total volume of fluids that comprises the wetting fluids and a second fraction of the total volume of fluids that comprises the non-wetting fluids, (c) defining a value for a flow rate of the total volume of fluids flowing through the Sample, (d) assessing properties of the wetting fluids and the non-wetting fluids, (e) defining initial conditions for saturation of the wetting fluids (Sw), saturation of the non-wetting fluids (Sn), inlet pressure of the wetting fluids (Pw) and inlet pressure of the non-wetting fluids (Pn), (f) setting conditions at the inlet face of the Sample wherein non-wetting fluids and wetting fluids enter the pores of the Sample in separate and distinct areas, and (g) calculating pressures, saturation, and velocity vectors internal to the Sample, (h) calculating flow rates of the non-wetting fluids (Qn) through the Sample, flow rates of the wetting fluids (Qw) through the Sample, and pressure at the outlet of the Sample, (i) repeating steps a) through h) for a predefined number of time increments, t, and (j) periodically adjusting the inlet pressures Pn and Pw using a feedback control algorithm wherein quasi-steady state values for Qn and Qw are achieved.

The present invention also relates to a system computing or determining or estimating fractional multi-phase, multi-component flow through a porous medium comprising (a) a scanner capable of producing a three dimensional digital image of a porous medium, (b) a computer comprising at least one processor operable for executing a computer program capable of classifying elements in the three dimensional digital image as solid (grain) and pore (void), (c) a computer comprising at least one processor operable for executing a computer program capable of performing the indicated computations, and (d) at least one device to display, print, or store results of the computations.

The present invention also relates to a computer program product on a computer readable medium that, when performed on a controller in a computerized device provides a method for performing one or more or all of the indicated computations.

The present invention also relates to use of the indicated method and/or system to calculate or estimate fractional multi-phase/multi-component fluid flow through porous media of a subterranean reservoir, such as a subterranean oil reservoir, and to calculate or estimate relative permeabilities at various levels of saturation, and use of the calculated or estimated relative permeabilities to provide improved evaluations and estimates of the productivity of the subterranean reservoir. The methods and systems of the present invention also can be used to provide numerically modeled evaluations of fractional multi-phase/multi-component fluid flow through other type of porous media.

It is to be understood that both the foregoing general description and the following detailed description are exemplary and explanatory only and are intended to provide a further explanation of the present invention, as claimed.

The accompanying drawings, which are incorporated in and constitute a part of this application, illustrate some of the features of the present invention and together with the description, serve to explain the principles of the present invention.

BRIEF DESCRIPTION OF DRAWINGS

FIGS. 5a-5f shows several views of the inlet face of the Sample with the pore area divided into sub-areas for wetting and non-wetting fluids, according to an example of the present application.

DETAILED DESCRIPTION OF THE PRESENT INVENTION

The present invention relates in part to a method for computing fractional, multi-phase/multi-component flow through a porous medium employing a three-dimensional (3D) digital representation of a porous medium integrated with a computational fluid dynamics (CFD) method of calculating flow rates, pressures, saturations, internal velocity vectors, and/or other flow parameters which can provide improved determinations, e.g., more rapid and/or accurate determinations, of fluid transport properties of the porous medium, such as calculating or estimating relative permeability versus saturation for imbibition and/or drainage. These determinations can be made without the need for expensive and time consuming laboratory experiments on physical samples of the porous medium. The method can employ a unique method of simulating the introduction of non-wetting and wetting fluids into the pores at the inlet face of the 3D digital representation of a porous medium and a process control application to achieve quasi-steady state flow at low inlet concentrations of non-wetting fluid. In addition, the method of the present invention reduces the time required to complete the fluid dynamic calculations. The resulting values of flow of non-wetting fluid, wetting fluid, saturation and other parameters can be used to generate plots of relative permeability imbibition and drainage curves. The ability to make these types of determinations on the fluid transports characteristics of the porous media can improve the accuracy of cost and technical decision-making made with respect to production on the porous media. Computerized systems and computer programs for performing the method are also provided.

Figure 3:
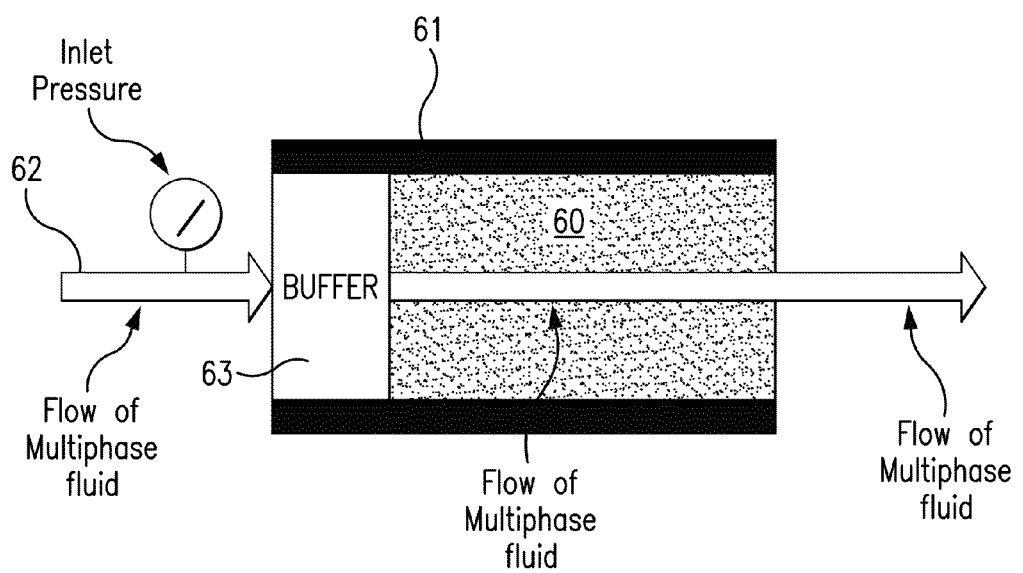
FIG. 3 is a schematic which is representative of physical laboratory methods, both steady state and unsteady state, which can be used to calculate or estimate multiphase and multi-component flow through a porous medium.

The method of the present invention can be used to calculate the flow of multi-phase, immiscible fluids through porous media, such as shown schematically in FIG. 3. For purposes of this invention, the term "multi-phase" refers to multiple phases of an element of compound such as liquid and vapor and to multiple compounds in a mixture such as oil and water. The fluids are categorized as wetting fluids and non-wetting fluids. Wetting fluids are those fluids that tend to cover or adhere to the interior surface of pores in the porous medium. Wettability is the tendency of one fluid to spread on, or adhere to, a solid surface in the presence of other immiscible fluids. Wettability is defined by the contact angle of the fluid with the solid phase. One example of the present invention describes a system comprising one wetting fluid and one non-wetting fluid. However, the methods described herein can apply to systems comprising multiple wetting and/or non-wetting fluids. The porous medium to which the methods described herein can be applied is not necessarily limited. The porous medium can comprise, for example, rocks; soils; zeolites; biological tissues such as bones, wood, cork and similar materials; cements; ceramics; compacted solid particles such as sand, clay, rock, ceramics, inorganic compounds, organic compounds, metals and similar materials; synthetic materials such as polymers; and other similar materials.

Figure 4:
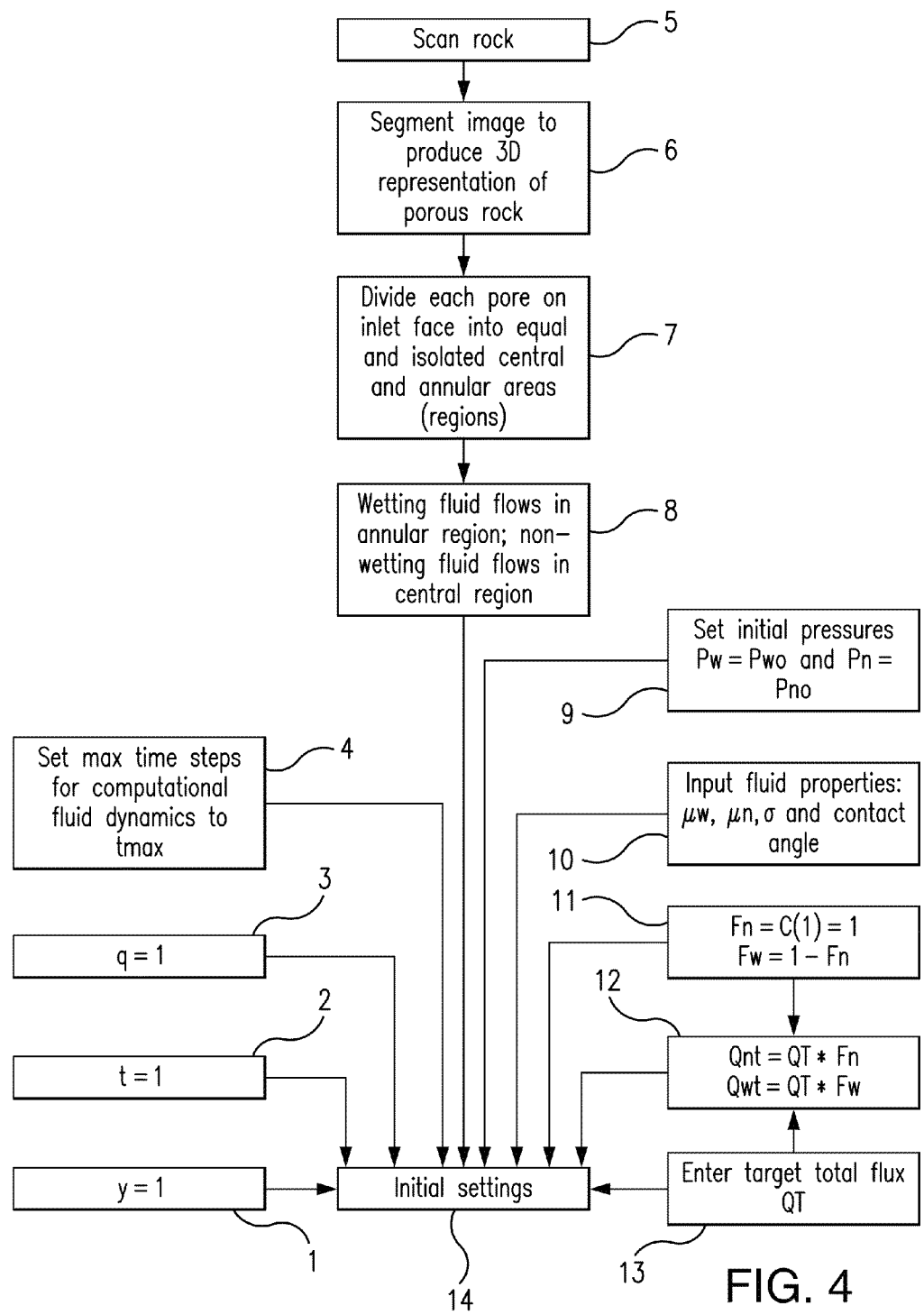
FIG. 4 is a flow chart showing how initial conditions for the simulation are set, according to an example of the present application.

In the following descriptions, references to parenthetical numbers (1) to (13) refer to the correspondingly numbered boxes shown in FIG. 4, references to parenthetical number (14) refer to the correspondingly numbered boxes shown in FIGS. 4 and 7, and references to parenthetical numbers (15) to (34) refer to the correspondingly numbered boxes shown in FIG. 7. Referring to FIG. 4, a physical sample from a porous medium can be scanned (5) with a device capable of producing a three-dimensional (3D) digital representation of the porous structure of the sample. The source of the sample, such as in the instance of a rock formation sample, is not particularly limited. For rock formation samples, for example, the sample can be sidewall cores, whole cores, drill cuttings, outcrop quarrying samples, or other sample sources which can provide suitable samples for analysis using methods according to the present invention. Devices such as a CT scanner can be used for this purpose where the sample is exposed to x-rays of a particular frequency. The frequency determines the resolution of the scan. Examples of suitable CT scanners for making images usable with methods according to the present invention include, for example, 3D tomographic x-ray transmission microscopes, such as MicroXCT-200 and Ultra XRM-L200 CT, which are made by Xradia, Inc. (Concord, Calif. USA). For very fine-grained porous media such as shales, the scans may be performed on a scanning electron microscope, SEM. The software supplied with the scanning machine tomographically reconstructs the 3D volume in an ordered array of voxels.

The segmentation process (6) classifies individual voxels as either solid or pore. A three-dimensional digital representation can be created of the Sample (porous medium), for example, which comprises multiple, ordered planes of voxels wherein each of the voxels can represent a pore (pore voxel) or solid (grain voxel). There may be more than one class of materials in the porous medium. The segmentation process is necessary due to the resolution of the scanner as compared to the size of the grains and pores in the porous medium. A number of methods to segment the 3D gray scale representation can be used for this purpose. One such method, for example, is described by Nur in U.S. Pat. No. 6,516,080, which is incorporated herein by reference in its entirety. Another gray scale and segmentation process which can be adapted for use in the present methods is U.S. Patent Application Publication No. 2010/0128932 A1, which is incorporated herein by reference in its entirety. Any method capable of producing a digital 3D representation of a porous medium can be sufficient for the present invention. After image segmentation (6), each pore on the inlet face can be divided into equal and isolated central and annular areas (regions)(7), and the sample is initially flooded with the wetting fluid (8), as is described in further detail in discussions of other related figures provided herein.

Initial settings (14) are shown in FIG. 4. In the present invention, the CFD method used can be the lattice Boltzmann method or other methods. Several indexes can be used in the method to control actions taken in the simulation. The parameter y is an index for the number of wetting/non-wetting fluid combinations to be run in the simulation. Initially the index y is set to 1 so that it points at the first composition to be simulated (1). The parameter t is an index for the number of time steps in the simulation. t is initially set to 1 (2). The parameter q is an index for the number of time steps at which feedback control action will take place, and q is initially set to 1 (3). The parameter tmax (4) is a value for the maximum number of time steps to be completed for each combination of wetting and non-wetting fluids to be run through the simulation. Fluid properties are required for the calculation of fluid flows and for calculation of relative permeability (10). The properties of the wetting fluids and non-wetting fluids which may be used in the calculations can comprise, for example, viscosity, contact angle, interfacial tension and other physical or chemical properties. Values of viscosity of the wetting fluid, $\mu w$, viscosity of the non-wetting fluid, $\mu n$, interfacial tension, $\sigma$, and contact angle are set. As also shown in FIG. 4, an initial value for Pw, the pressure exerted on the wetting fluid, and Pn, the pressure exerted on the non-wetting fluid, are input (9). Values for the fraction of non-wetting fluid Fn and wetting fluid Fw which enter the inlet face of the sample, also are initially set (11). The user inputs a total desired flow rate, QT, typically measured in meters per second or feet per day or any other desired units, to be forced through the Sample (13), and initial Qwt and Qnt values are determined (12), which are calculated flow rates of wetting and non-wetting fluids, respectively.

As shown in FIG. 3, a Sample (60) is subjected to a wall boundary condition as represented by the thick black lines (61) such that a multiphase fluid may be forced through the Sample by a pressure gradient (62). The Sample can comprise an inlet face and an outlet face wherein the inlet and outlet faces are parallel to each other and three or more surfaces orthogonal to the inlet face and the outlet face wherein the three or more orthogonal surfaces are impervious to flow of the wetting fluids and the non-wetting fluids. Because the wetting fluid and non-wetting fluid entering the sample may be at different pressures, an extraneous back flow condition may occur at the inlet where some fluid may exit the sample. In the case where a back flow condition occurs, a buffer zone or region (63) at the Sample inlet can be used to eliminate the extraneous flow back. The buffer zone or region can alter calculations for at least 1 or 2 or 3 or more layers of voxels that make up the Sample starting from the inlet face. For example, the inlet face can comprise a buffer zone parallel to the inlet face comprising one voxel plane, 2 voxel planes, 3 voxel planes or more. The Sample is used in a computational fluid dynamics calculation to estimate flow rates of the wetting and non-wetting fluid through the Sample and to compute the relative permeability of the porous medium for specific saturations on the interior of the Sample.

Figure 7:
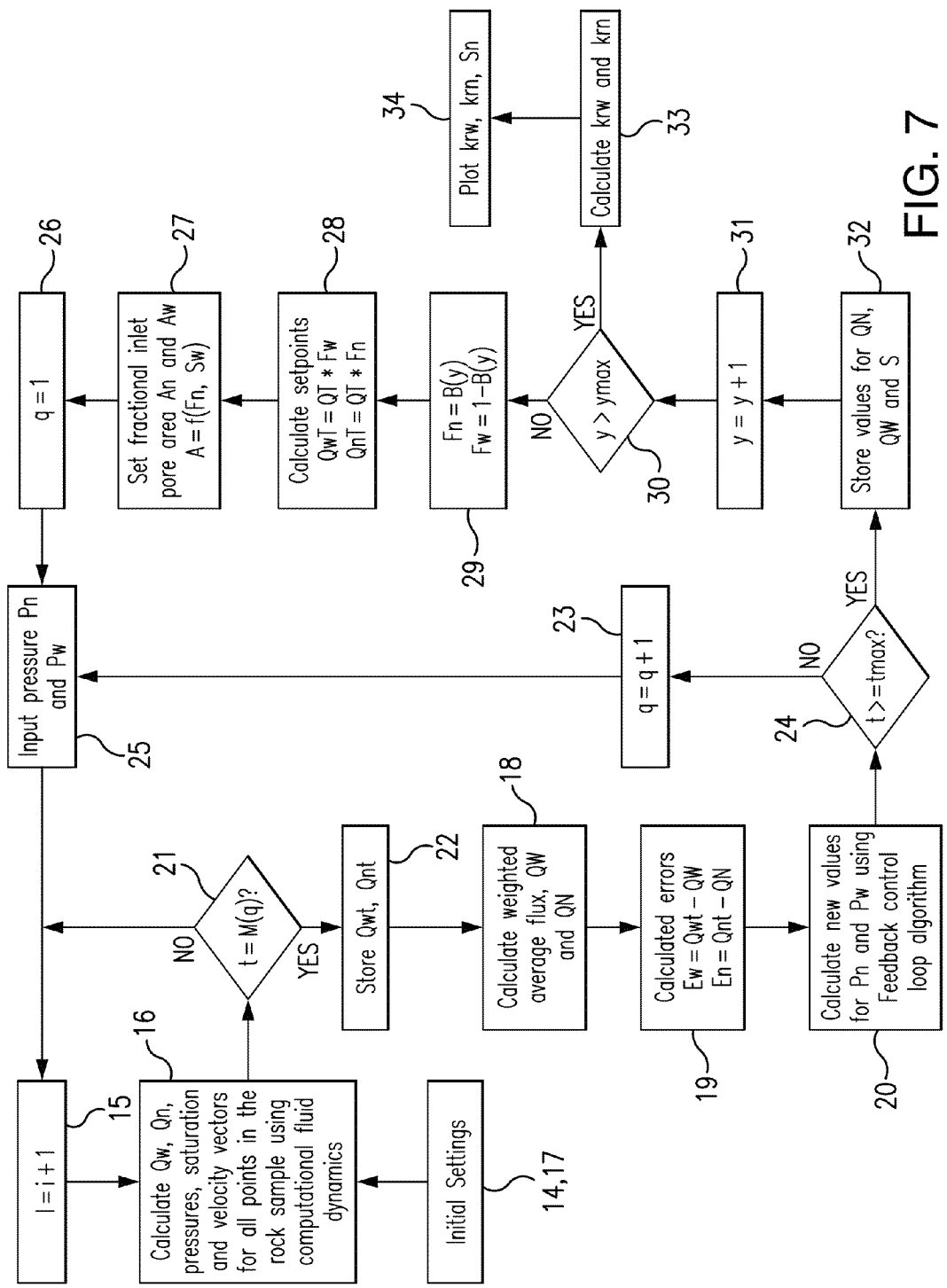
FIG. 7 is a process flow diagram of a numerical simulation method for calculating or estimating fluid transport properties including relative permeabilities and saturations of a porous medium, according to an example of the present application.

Referring to FIG. 7, once initial settings (17) have been established, such as described with respect to settings (14) shown in FIG. 4, the simulation can begin by calculating flow rates of wetting and non-wetting fluids, pressures, saturation levels, velocity vectors and other properties for all points located in the Sample using computational fluid dynamics (CFD) calculations (16). The CFD calculations are repeated for a discrete number of time intervals, t (15). At specific time intervals, shown as t=M(q) (21), values of wetting and non-wetting fluid flow are stored (22) and a weighted average flow for the wetting and non-wetting fluids are calculated and stored (18). The weighted average fluid flows are compared to the desired or set point values of wetting fluid flow and non-wetting fluid flow to produce an error (19) that is then used to calculate new values of the wetting fluid pressure and non-wetting fluid pressure at the inlet face of the Sample (20). Until tmax is reached (24), an index is advanced to point to the next time that feedback control calculations should be made (23), and the new pressures for wetting fluid and non-wetting fluid at the inlet are input into the CFD calculations (25). For example, a check is made to see if the simulation has reached quasi-steady state, for example, by checking to see if the pre-defined maximum number of time increments, tmax, has been reached (24), or by other methods indicated herein. If tmax has been reached, calculated values of weighted average flows of wetting and non-wetting fluids as well as other properties such as fluid saturation can be stored at this point (32) and used to calculate other properties of interest such as relative permeability (33). This simulation can optionally continue for a number of additional compositions of wetting and non-wetting fluids to be forced through the Sample (30), (31). New values for the fraction of wetting fluid, Fw, and non-wetting fluid, Fn, which enter the inlet face of the sample, can be selected (29) and new flow set points for wetting fluid and non-wetting fluid calculated (28). When the fraction of wetting fluid and non-wetting fluid change, the fractional inlet pore area used for wetting and non-wetting fluid can be changed (27). The fraction of inlet pore area for wetting fluid and non-wetting fluid is a function of the fraction of non-wetting fluid entering the inlet face of the Sample. In general, the fractional area for non-wetting fluid should be decreased when the fraction of non-wetting fluid entering the inlet face of the sample is less than about 10% by volume, or less than about 20% by volume, or less than 30% by volume. In the case where multiple combinations of wetting and non-wetting fluids are forced through the Sample, relative permeability versus saturation curves can be plotted (34).

As an example, the present invention simulates two-phase flow through porous media. FIGS. 5a-5f show six images, respectively, of the inlet face of the Sample. In FIG. 5a the pores at the inlet face are filled with the non-wetting fluid shown in darker shading 52. If a non-wetting fluid or two phase fluid is then forced through the sample, the distribution of wetting and non-wetting fluid at the inlet face is critical to the CFD simulation producing a representative result and also critical to achieving quasi-steady state flow through the Sample. One of the inlet conditions required for the CFD simulation is the area of the pores at the inlet face that is allocated for wetting fluid flow and the area of the pores at the inlet face that is allocated for non-wetting fluid flow and the distribution of the areas for wetting fluid flow and non-wetting fluid flow. In the present invention, the area for wetting fluid at the inlet is first distributed at the internal face of the pores as a single layer of voxels in the digital Sample as shown in the white areas 53 in FIGS. 5b-5f. The percentage of wetting fluid area may be increased by adding more voxels in a layer-wise manner. FIGS. 5a through 5f show increasing area for the wetting fluid up to about 50% which is depicted in FIG. 5f.

Figure 6B:
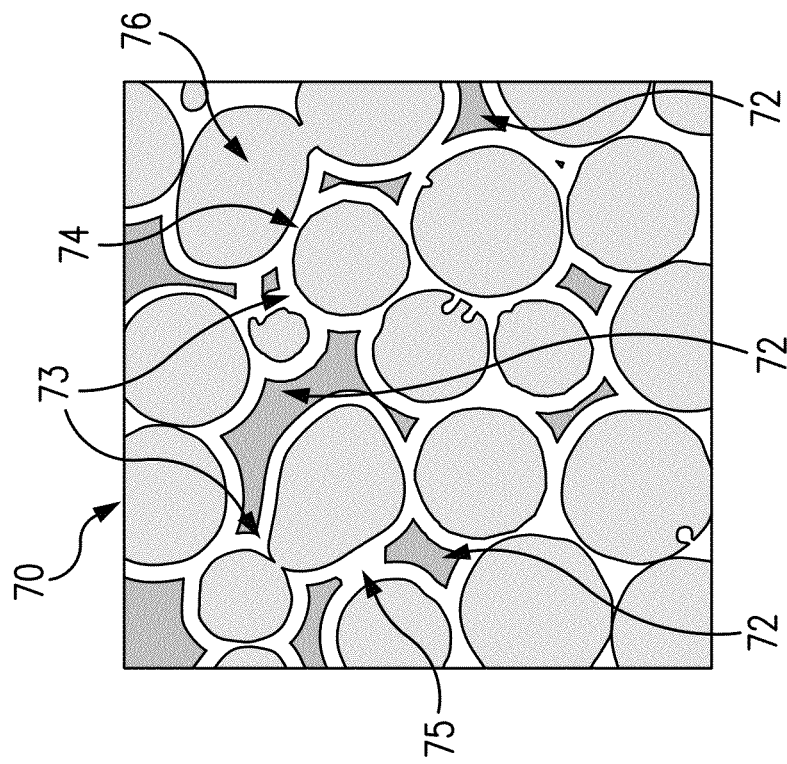
FIGS. 6a and 6b show the detail of the inlet face of the Sample with the pore area divided into sub-areas for wetting and non-wetting fluids, according to an example of the present application.
Figure 6A:
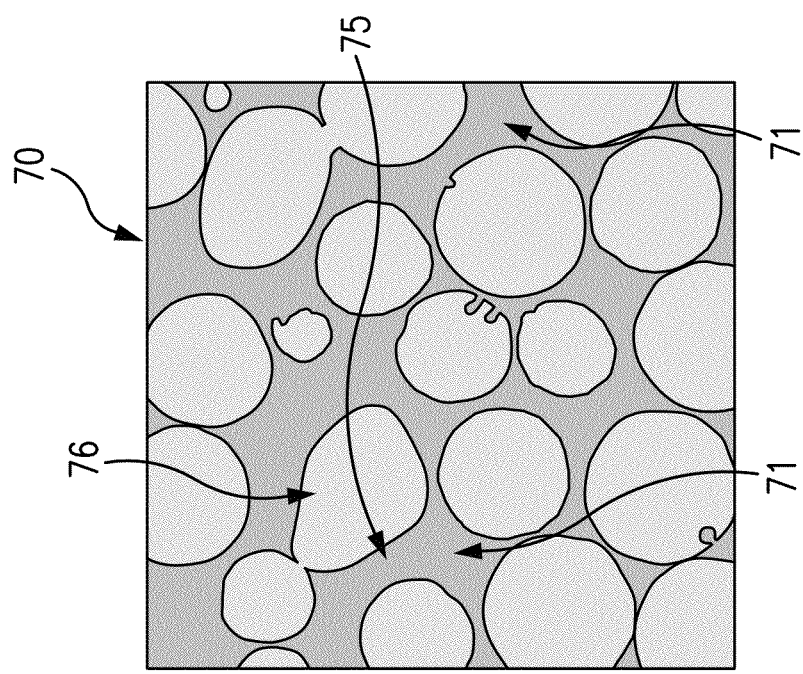

The inlet face (70) of the Sample is shown in FIGS. 6a and 6b. The non-wetting fluids and the wetting fluids can enter the Sample through pores on the inlet face of the Sample. The image on the left is the Sample as shown in FIG. 5a and the image on the right is the same as shown in FIG. 5f. The image in FIG. 6a on the left shows a porous rock in which the pores filled with non-wetting fluid are shown in darker shading. The grains or solid rock (76) are shown in intermediate shading. The face of the Sample has pores (71) through which a two-phase fluid enters the sample. Each pore area is divided into sub-areas. One area (73) represents the annular area, Aw, through which the wetting fluid flows. A second area, An, (72) represents the central area through which the non-wetting fluid flows. Because the image is digital, the creation of the area, Aw, is done by selecting voxels adjacent to the grains and designating them as an area for wetting fluid. This is an accurate representation of the real world as the wetting fluid has an attraction to the solid surfaces in the rock. The voxels are layered starting with the voxels closest to the grain boundaries first. The remaining voxels (72) are designated as An. This is also an accurate representation of the real world because the non-wetting fluid is immiscible with the wetting fluid and surface tension and capillary pressure will force the non-wetting fluid into the interior space of the pore and away from the solid surface. Notice the area of the Sample face labeled (75). This is an example of the 3D character of this separation. The inlet face of the Sample is a digital slice of the porous medium. Immediately behind the inlet face is another plane. At location (75), the plane behind the inlet face is a solid or rock at location (75) so the area at that location becomes effectively an area for the inlet flow of wetting fluid. This area (75) is defined in exactly the same manner, by layering voxels designated as Aw at the grain boundary, but in this case, the grain boundary is in the direction perpendicular to the Sample inlet face. The two areas An and Aw are separated by a boundary (74) such that the two fluids are decoupled. The two areas (72) and (73) are initially set approximately equal to each other. In this case the fractional area center portion of the pores on the inlet face, An, and the fractional area of the annular portion of the pores on the inlet face, Aw, are approximately equal. So, in this initial case, An is about 0.5 and Aw is about 0.5. The ratio of these two areas may be adjusted to compensate for the condition when the flow rate of non-wetting fluid is less than about 50% by volume of the total flow through the sample or less than about 10% by volume of the total flow through the sample or less than about 1% by volume of the total flow through the sample. In the case where a single phase is injected into the Sample, the area An is set to 1 in the case of a non-wetting fluid and the area Aw is set to 1 in the case of a wetting fluid. The inventors have found that setting and controlling the ratio An to Aw results in convergence of the CFD calculations used to calculate the fractional flow at different saturation levels.

The Sample is initially flooded with either the wetting or non-wetting fluid to totally saturate the sample. As one option, the sample is initially flooded with the wetting fluid (8) (referring to FIG. 4). This provides an initial internal boundary condition for the simulation.

As indicated, the user inputs a total desired flow rate, QT, typically measured in meters per second or feet per day or any other desired units, to be forced through the Sample (13). The total flow rate input can be based on the need of the technician doing the simulation, typically a geologist or reservoir engineer. The input flow rate may be an existing total flow rate from a well or a desired well flow rate, for example.

Each of the two fluids, wetting and non-wetting, are subjected to different pressures. As indicated, an initial value for Pw, the pressure exerted on the wetting fluid, and Pn, the pressure exerted on the non-wetting fluid are input (9). Darcy's law can be used, for example, to make an initial estimate of pressure with the following equation [11]:

$$P_i = \frac{\mu \cdot L \cdot Q}{k_{abs} C \cdot A} \quad [11]$$

where
$P_i$=initial value for pressure of the desired phase, wetting or non-wetting
$\mu$=viscosity of the desired phase
L=length of the Sample in the flow direction
Q=desired flux of the desired phase
$k_{abs}$=absolute permeability of the Sample
A=area of the Sample inlet face
C=constant The simulation converges more rapidly when initial values of Pw and Pn are lower than the final value. Therefore values of the constant, C, can be about 20, or about 30, or about 40, or about 50, or higher values.

In the present invention, the non-wetting fluid can be forced through the pores on the inlet face of the Sample to displace the wetting fluid (8). Alternatively, if the Sample was initially saturated with the non-wetting fluid, then the wetting fluid can be initially forced through the pores on the face of the Sample. Because optionally there is no wetting fluid being forced through the Sample, the center fractional area of the pores, An, can be set to 1. When these conditions are used, there is only single-phase flow at the Sample inlet. However, because the Sample was initially flooded with wetting fluid, there is two-phase flow on the interior of the Sample and at the Sample outlet after a transient time period. As an option, the initial Sample saturation is a total wetting fluid saturation, Sw=1.0, and a total non-wetting fluid saturation, Sn=1.0. As another option, the initial Sample saturation can be the ending saturation conditions from a previous simulation.

The CFD calculations can be executed in discrete increments as shown in FIGS. 5(a)-(f). Each increment is mapped to time increment t, wherein t can be, for example, seconds, milliseconds or other time units. For each time increment, key parameters of the flow through the Sample (16) are calculated. The key parameters can include, for example, the integrated flow rate of the wetting fluid over the Sample volume, V, at a given time $$t, Qwt = \frac{1}{V} \int_V Qw,$$

the integrated flow rate of the non-wetting fluid over the Sample volume, V, at a given time t, $$Qnt = \frac{1}{V} \int_V Qn,$$

and the internal pressures, velocity vectors for each phase and the saturations for each voxel in the Sample at a given time t. The time step indicator, t, is incremented by 1 each time the key parameters are calculated (15). Fractional flow rates can be determined based on calculations which comprise use of the above equations as used for determining Qwt and Qnt, wherein the sample volume (V) can be for the whole volume of the original sample or alternatively for a fraction of the original whole volume. The fraction of the volume can be chosen, for example, close to the inlet to minimize the time-lag of the control.

Periodically, the number of time steps elapsed is checked to see if feedback control calculations are to be made (21) (referring to FIG. 7). The feedback control calculations are made periodically based on a list of pre-defined total time increments elapsed (21), where M(q) is the sequence of q time steps at which control action is taken. Corrections are made to the inlet pressures, Pw and Pn, such that the target flow rates QwT and QnT are achieved (20). The corrections are made, for example, with a feedback control algorithm. The corrections can be periodic adjustments of the inlet pressures set to occur, for example, about once every 10 time increments, or once every 100 time increments, or once every 500 time increments, or once every 1,000 time increments, or once every 10,000 time increments, or more. A unique characteristic of the present invention is the use of a feedback control algorithm in a computational fluid dynamics algorithm for two phase fluid flow through porous media to establish fractional fluid flow. The total number of corrections can range, for example, from about 100 to 500, or from about 10 to 1000, or any other range as required to achieve quasi-steady state flow. As an option, the number of time increments of subsequent periodical adjustments of inlet pressure can be different. For example, the periodical adjusting of inlet pressures can occur more often in the first half of the total time of the simulation than in the second half of the simulation. More corrections may be made early in the simulation than later in the simulation because the errors in QwT and QnT tend to be larger in the early portion of the simulation. The number of feedback corrections in the first half of the simulation time can be, for example, about 10, or about 15, or about 20 or more times the number of corrections made in the second half of the simulation time. The number of corrections may continuously vary through the course of the simulation, for example, with more corrections being made early in the simulation compared to later in the simulation.

Qwt and Qnt are the calculated flow rates of wetting and non-wetting fluids, respectively, for time interval t. For each time increment that feedback control corrections are made, the values of Qwt and Qnt are stored (22) and a moving time or weighted time average of the stored values of flux of wetting fluid at time t, QW, and the non-wetting fluid at time t, QN, is calculated (18). The weighted average, such as used for QW, QN, or QT, can be, but is not limited to, an arithmetic weighted average, a geometric weighted average, or a harmonic weighted average. The moving average, such as used for QW, QN, or QT, can be, but is not limited to, a simple rolling average or an exponentially weighted moving average.

As shown in FIG. 7, new values for Pn and Pw are calculated (20) using a feedback control algorithm. As an option, the feedback control algorithm can comprise a separate feedback control algorithm to set the inlet pressure for the wetting fluid and a separate feedback control algorithm to set the inlet pressure for the non-wetting fluid, where the inlet pressure for the wetting fluid and the inlet pressure for the non-wetting fluid are set independently. The feedback control algorithm can comprise, for example, one feedback control algorithm to set the inlet pressure for both the wetting and the non-wetting fluids, where the inlet pressure for the wetting fluid and the inlet pressure for the non-wetting fluid are equal. The present invention can use a negative feedback control algorithm wherein errors, Ew and En (19), are calculated by subtracting the actual value, QW and QN, from the target value, QwT and QnT. The present invention can use two proportional-integral-derivative (PID) control algorithms, one to control the flow of the wetting fluid fraction and the other to control the flow of the non-wetting fluid fraction. In the case of PID control the integral and derivative of the errors Ew and En are calculated at each time step t in a way to define the output of the PID controller, πw and πn. The output of the PID control is used to define the variation of the pressure from its initial value (9), so that for each phase (wetting and non-wetting in the case of double control) the new pressure is Pw=Pi+Pi*πw, and Pn=Pi+Pi*πn, where Pi*π is the variation of the pressure each time that the controller is activated. The initial pressure value sets the scale of both the pressure and its variation. For example, the PID control loop can comprise an input error Ew and output a new inlet pressure, Pw, wherein Pw=Pi+Pi*πw, Pi=the initial pressure set at the beginning of the simulation, πw=f(Ew) such as $$K_P*Ew + K_I \int Ewdt + K_D \frac{dEw}{dt},$$

$K_P$=proportional control constant, $K_I$=integral control constant, and $K_D$=derivative control constant. Where the PID control loop comprises an input error En and outputs a new inlet pressure, Pn, Pn=Pi+Pi*πn, Pi=the initial pressure set at the beginning of the simulation, and πn=f(En) such as $$K_P*En + K_I \int Endt + K_D \frac{dEn}{dt},$$

wherein $K_P$, $K_I$, and $K_D$ represent the same indicated constants. Other control algorithms, such as adaptive control, hierarchical control, intelligent control, optimal control, robust control, neural network control, fuzzy logic control, or stochastic control, can be employed as alternatives.

Figure 8A:
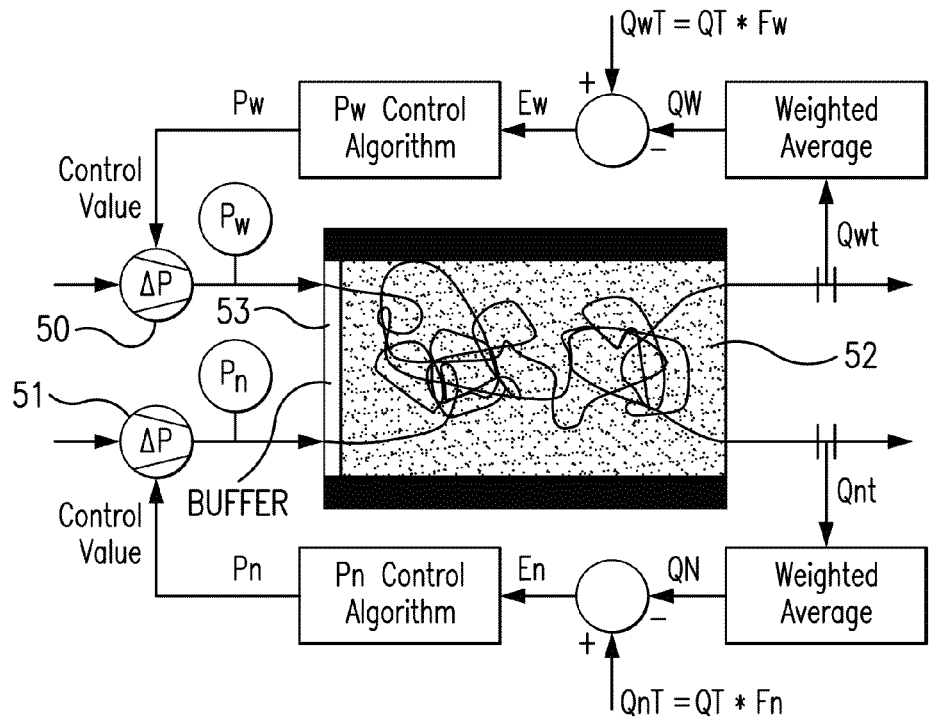
FIGS. 8a and 8b are diagrams outlining the process control scheme for the flow of wetting and non-wetting fluid, according to an example of the present application.

In FIG. 8a, the pressure of the wetting fluid is digitally raised by a digital representation of a device to increase pressure (50) and the pressure of the non-wetting fluid is digitally raised by a digital representation of a device to increase pressure (51). Both fluids are thus forced through the Sample (52).

In FIG. 8a, the pressure of wetting fluid, Pw, and the pressure of the non-wetting fluid, Pn, are different in most cases. Because of this pressure difference, the simulation may calculate backflow for the wetting or non-wetting fluid. Backflow is a circumstance wherein fluid flows out of the Sample due to the difference in applied pressures of wetting and non-wetting fluids. Backflow is an extraneous effect of the pressure differences at the inlet and does not occur in a physical test. Therefore, to compensate for this factor, the present investigators have provided a unique technique wherein a buffer zone at the inlet (53) is created where the fluids cannot backflow. The buffer zone is made up of a number of voxel planes at the inlet where the number of voxel planes can be, for example, 1 or 2 or 3 or more. To assure that there will be no backflow in the buffer zone, the interfacial tension between the wetting and non-wetting fluid is set to zero and the viscosities of the wetting and non-wetting fluids are greatly increased. For example, the interfacial tension between the wetting fluid and non-wetting fluid can be set to zero for all calculations within the buffer zone. The viscosities can be increased by a factor of about 10 times, or about 20 times, or about 30 times, or about 40 times, or about 50 times or more. Other techniques to address backflow can also be developed and used.

The integrated or calculated flow of the wetting fluid over the Sample volume, Qwt, and the integrated or calculated flow of the non-wetting fluid over the Sample volume, Qnt, are measured and the (weighted) average flow of wetting fluid, QW, and the (weighted) average flow of non-wetting fluid, QN, are computed. The error between QW and the target flow of wetting fluid is calculated, Ew=QwT−QW and the error between QN and the target flow rate of non-wetting fluid is calculated, En=QnT−QN. The errors, Ew and En, are inputted into two separate control algorithms to adjust the inlet pressures Pw and Pn. The use of two separate control algorithms, one for wetting fluid and another for non-wetting fluid, results in simulations that better reflect the actual distributions of wetting and non-wetting fluids in a real-world sample.

Figure 8B:
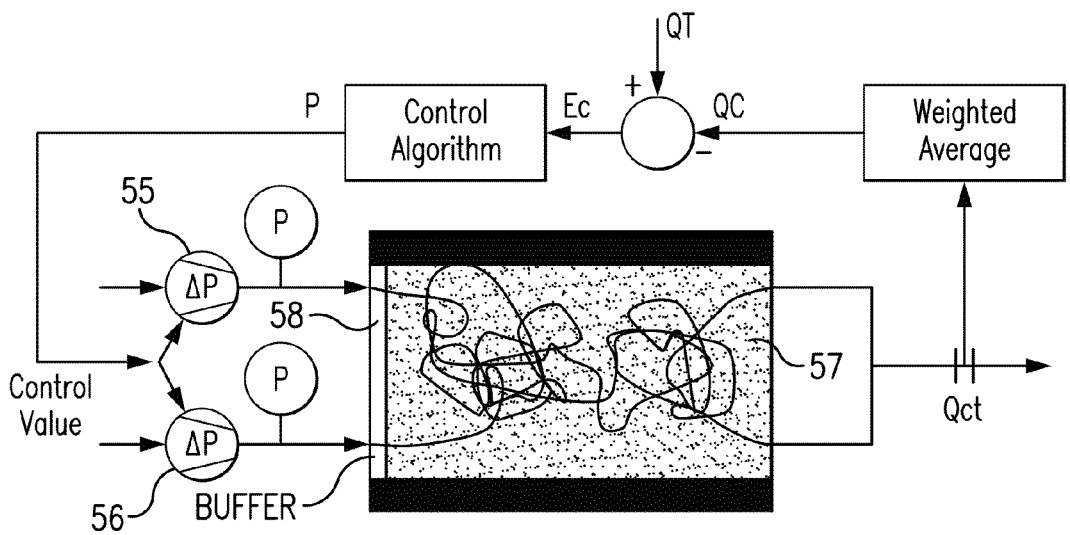

An alternative control scheme is shown in FIG. 8b where a single controller is used. In this case, the pressure of wetting and non-wetting fluid at the inlet is always the same. The pressure of the wetting fluid is digitally raised by a digital representation of a device to increase pressure (55) and the pressure of the non-wetting fluid is digitally raised by a digital representation of a device to increase pressure (56). Both fluids are thus forced through the Sample (57).

In FIG. 8b, the pressure of wetting fluid, Pw, and the pressure of the non-wetting fluid, Pn, are the same. There is no backflow when there is no pressure difference between wetting and non-wetting fluid. However, to ensure there is no calculated intermixing of wetting and non-wetting fluids at the inlet, a buffer zone at the inlet (58) can be created similar to the case where two separate controllers are used. As indicated, the buffer zone can be made up, for example, of a number of voxel planes at the inlet where the number of voxel planes can be 1, or 2, or 3 or more. To assure that there will be no intermixing in the buffer zone, the interfacial tension between the wetting and non-wetting fluid can be set to zero. There is no need to alter viscosities in the case of one controller because there is no pressure difference to drive backflow.

The integrated flow of the combined wetting and non-wetting fluids over the Sample volume, Qct, is measured and the weighted average flow of the combined wetting and non-wetting fluids, QC, is computed. The error between QC and the total target flow through the Sample, QT, is calculated, Ec=QT−QC. The error, Ec, is inputted into a single separate control algorithm to adjust the inlet pressure. For example, the PID control loop can comprise an input error Ec and output a new inlet pressure, Pc, wherein Pc=Pi+Pi*πc, Pi=the initial pressure set at the beginning of the simulation, and πc=f(Ec) such as $$K_P * Ec + K_I \int Ec \, dt + K_D \frac{dEc}{dt},$$

wherein $K_p$, $K_I$, and $K_D$ represent the same indicated constants. Using a single controller does not produce simulation results as representative of the real world as using two separate controllers. However, simulations using one controller are less complex, run faster and may produce results that are sufficiently representative in many cases. Single controller simulations can also be used for initial approximations of fractional multi-phase/multi-component flows through porous media. A PID control loop, for example, can be used in determining at least one or more, or all, of Ew, En, and Ec.

In the case of a PID control algorithm, there can be three controller settings: proportional gain ($K_p$), integral gain ($K_i$), and derivative gain ($K_d$). PID control loops are tuned by adjusting selecting values for $K_p$, $K_i$, and $K_d$ to achieve the desired control response. Values for $K_p$, $K_i$ and $K_d$ can be selected by any of the known tuning methods such as manual tuning, Ziegler-Nichols, Cohen-Coon, and other methods.

As indicated, the simulation runs for a sufficient number of time increments, tmax (24), to achieve quasi-steady state. The number of time increments (tmax) used can be a preselected value or a nonselected value that is triggered by a prescribed statistical threshold being met by certain computational results. The number of time increments may be set experimentally or by quantitative statistical methods. Quasi-steady state means that the calculated values of Qn, Qw, Pn, Pw and/or saturation do not vary by more than a pre-determined value within a fixed number of time steps. For example, at quasi-steady state, the variation in parameter values between consecutive time increments t or another selected number of increments t, such as for QN, QW, Pw, Pn, saturation, or other parameters, does not vary by more than a pre-specified value or threshold value. As an indicated option, tmax (24) can be a predefined number. As an option, the predefined number of time increments, t, can be set sufficiently large to achieve quasi-steady state. The present invention has found, for example, that setting tmax to a sufficiently large number can achieve quasi-steady state. The magnitude of tmax needed in this respect can depend upon the characteristics of the porous medium and the properties of the fluids flowing through the porous medium. The number of time increments can be, for example, set to a value of 10,000 or a higher value, or 100,000 or a higher value, or 1,000,000 or a higher value, or other values. In general, smaller pore structures and higher viscosity ratios between fluids can require larger values of tmax. As another option, the number of time increments for tmax can be a value that is contingent on certain calculated results meeting some numerical variance threshold (Vt). The pre-specified amount or variance threshold value (Vt) can be set at any desired value. For example, the variance threshold value (Vt) can be a percentage difference with respect to two or more consecutive calculated values for selected parameters. When the variance threshold (Vt) is calculated to be met, t becomes tmax (24) in that iteration, and the process proceeds to step 23. As an option, a threshold value (Vt), which can used to determine if quasi-steady state conditions have been reached in an iteration according to the present method, can be a value of about ±10%, or about ±7%, or about ±5%, or about ±3%, or about ±1%, or about ±0.5%, or other values. For example, if a variance threshold of ±5% is selected and applied to all parameters of interest, e.g., Qn, Qw, Pw, Pn, Sw, Sn and so forth, in the simulation method, and each parameter had a first normalized value of 100 at $t_1$ and a second normalized value in the range of 95-105 at $t_2$, then the ±5% threshold for finding quasi-steady state conditions would be met, and the method proceeds to step 32 shown in FIG. 7. In another option, the simulator can be designed to check to see if the selected threshold is met in more than one consecutive iteration before proceeding to step 32 shown in FIG. 7. Fractional multi-phase, multi-component fluid through porous media tends by nature to vary over time and typically does not reach a true or absolute steady state. Nevertheless, determinations of properties at quasi-steady state in the present methods have been found to be useful and advantageous for efficiently and accurately estimating fluid transport properties useful for evaluating porous media. As indicated, the achievement of quasi-steady state can be determined in the present methods, for example, by observation, experience of the person running the simulation, or quantitative methods that examine variance, rolling averages, or other assessments of QN, QW, Pw, Pn, saturation or other parameters.

As shown in FIG. 7, if tmax has not been reached (24), then the index for control action is incremented by 1, q=q+1 (23)

and the new values for Pn and Pw calculated in the feedback control algorithm are input to the CFD calculations (25). Steps (15), (16) and (17) are repeated until another control action is scheduled (21).

When tmax has been reached (24), final values for QN, QW and Sw are stored (32). Relative permeability can be calculated at this point from QN, QW, Sw and the fluid data and rock properties. The relative permeability at this point can be the imbibition relative permeability at the irreducible wetting fluid saturation, Swim This is a result of the way the simulation is run, starting with the Sample flooded with the wetting fluid and then replaced with the non-wetting fluid. Because of surface tension and wettability, all of the wetting fluid usually cannot be purged and the remaining wetting fluid is the irreducible wetting fluid for the Sample and fluids in the simulation. As an option, a method for calculating relative permeability of wetting and non-wetting fluids flowing through a porous medium can comprise (a) defining a series of pairs of non-wetting fluids and wetting fluids, each pair to be forced through the Sample, such as described herein; (b) setting initial Sample saturation; (c) forcing each pair of non-wetting and wetting fluids through the Sample, such as described herein; (d) recording calculated values of QN, QW and wetting fluid saturation, Sw for each pair of wetting and non-wetting fluids; (e) calculating values of relative permeability of the wetting fluid, kw; calculating values of the relative permeability of the non-wetting fluid, kn; and calculating values of the water saturation, Sw, and (f) generating a plot of values of kw and kn versus Sw. The initial Sample saturation can be, for example, total wetting fluid saturation, Sw=1.0, total non-wetting fluid saturation, Sn=1.0, or any other saturation. As another option, the initial Sample saturation can be the ending saturation conditions from a previous simulation.

Following the initial time steps where the non-wetting fluid is forced through the Sample, several combinations of wetting and non-wetting fluids are forced through the Sample as described above and shown in blocks (15), (16), (21), (22), (18), (19), (20), (24), (23), and (25) in FIG. 7. The index for feedback control action, q, is reset to 1 (26). To perform the simulation with the new combination of wetting and non-wetting fluid, new values for the fraction of wetting fluid, Fn, and the fraction of non-wetting fluid, Fn, can be selected from the list of fluid combinations pre-defined (29). The number of pairs of values for Fn and Fw can be, for example, 10, or 20, or more. Any combination of Fn and Fw can be used where the sum of them is equal to 1 (i.e., Fn+Fw=1). The sum of Fn and Fw represents 100% of the fluid (non-wetting fluid and wetting fluid) which enters the inlet face of the sample. The pairs of values, Fw and Fn, stored in the list, B(y), as an option, can be:

a) [0.8, 0.2]; [0.6, 0.4]; [0.4, 0.6]; [0.2, 0.8]; [0, 1]; [0.2, 0.8]; [0.4, 0.6]; [0.6, 0.4]; [0.8, 0.2]; [1, 0], or
  b) [0.9, 0.1]; [0.85, 0.15]; [0.8, 0.2]; [0.75, 0.25]; [0.7, 0.3]; [0.6, 0.4]; [0.5, 0.5]; [0.4, 0.6]; [0.3, 0.7]; [0.25, 0.75]; [0.2, 0.8]; [0.85, 0.15]; [0.1, 0.9]; [0, 1];
    [0.1, 0.9]; 9.15, 0.85]; [0.2, 0.8]; [0.25, 0.75]; [0.3, 0.7]; [0.4, 0.6]; [0.5, 0.5]; [0.6, 0.4]; [0.7, 0.3]; [0.75, 0.25]; [0.8, 0.2]; [0.85, 0.15]; [0.9, 0.1]; [1, 0], or
  c) other combinations.

As an option, the ratio (R) of the viscosities of the low viscosity phase to the high viscosity phase of the wetting and non-wetting fluids can be used to scale the pairs of values, Fn and Fw, and the resulting scaled values thereof, Fn' and Fw', can be stored in the list, B(y), in substitution for values Fn and Fw. The wetting fluid viscosity ($\mu w$) can be high or low. The non-wetting fluid viscosity ($\mu n$) also can be high or low. The ratio (R) can be $\mu w/\mu n$ or $\mu n/\mu w$, depending on which viscosity is lower and which is higher. That is, the lower of the wetting fluid viscosity ($\mu w$) and the non-wetting fluid viscosity ($\mu n$) can be used as the numerator in the ratio and the other viscosity is used as the denominator value. For example, where wetting fluid viscosity is high and non-wetting fluid viscosity is low, then the ratio (R) would be non-wetting fluid viscosity/wetting fluid viscosity ($\mu n/\mu w$). Where the wetting fluid viscosity is low and non-wetting fluid viscosity is high, then the ratio (R) would be wetting fluid viscosity/non-wetting fluid viscosity ($\mu w/\mu n$). For example, for pairs of (Fn', Fw'), Fn' can be calculated as the value of (Fn×R) and Fw' is calculated as the value of (1−(Fn×R)), wherein R is the ratio of viscosities of the indicated low viscosity phase/high viscosity phase. Any combination of Fn' and Fw' has a sum that is equal to 1. The sum of Fn' and Fw' represents 100% of the fluid (non-wetting fluid and wetting fluid) which enters the inlet face of the sample. An example of pairs of values, Fn' and Fw', calculated and stored in the list, B(y), for example, can be:

a) [R, 0]; [(0.9*R), (1−0.9*R)]; [(0.8*R), (1−0.8*R)].

The pairs of values for Fw and Fn indicated above cover simulation of imbibition and drainage curves as shown in FIGS. 5(*a*)-(*f*). As an option, the pairs of non-wetting and wetting fluid can comprise an ordered series of values in which Fn decreases in steps to zero and then increases to 1.0. The present invention is unique in its ability to simulate and digitally compute imbibition and drainage curves with a high degree of accuracy due in part to the inlet boundary conditions establishing separate areas for wetting and non-wetting fluids at the inlet and the unique process control approach that make convergence of the calculations robust and practical from a computation time standpoint.

Fractional inlet pore areas for non-wetting fluid, An, and wetting fluid, Aw, can be adjusted for each combination of wetting and non-wetting fluid. Fractional areas which are approximately equal to 0.5 and Aw approximately equal to 0.5 are acceptable for many combinations of Fn and Fw. However, for low values of Fn, the fractional area An may need to be reduced and the corresponding fractional area Aw increased. An+Aw add up to 1.0. An may need to be reduced when fractional flow becomes too low with respect to the available area to fully fill the available central area of the pores. This can result in instability and trapping and release of large bubbles of non-wetting fluid in the simulation that do not satisfy the required flow rate. As an option, the pores on the inlet face can comprise separate and distinct areas formed by allocating pore voxels immediately adjacent to a grain voxel for the flow of the wetting fluids (Aw) and the remaining pore voxels are allocated for the flow of the non-wetting fluids (An). The Aw may be increased, for example, by further allocating pore voxels adjacent to Aw for the flow of the wetting fluids (Aw) and the remaining pore voxels are allocated for the flow of the non-wetting fluids (An). As an option, Aw and An can be provided, wherein the (sum of voxels in An)/((sum of voxels in An)+(sum of voxels in Aw)) is approximately 0.5 or less. As an option, the fractional area of the pores on the inlet face allocated for injection of non-wetting fluid, An, is decreased when Fn is less than about 0.2, or when Fn is less than about 0.1, wherein An is reduced to about 0.4 or less, or about 0.3 or less, or about 0.2 or less, or about 0.1 or less, or other values. Adjusting the fractional areas An and Aw is a unique characteristic of the present invention, which makes it possible for the simulations to achieve quasi-steady state and produce useable results.

Target flow rates for the new fractional flows can be calculated (28) as follows:

$$Q_wT = QT * F_w \qquad \text{a)}$$

$$Q_nT = QT * F_n. \qquad \text{b)}$$

Figure 1:
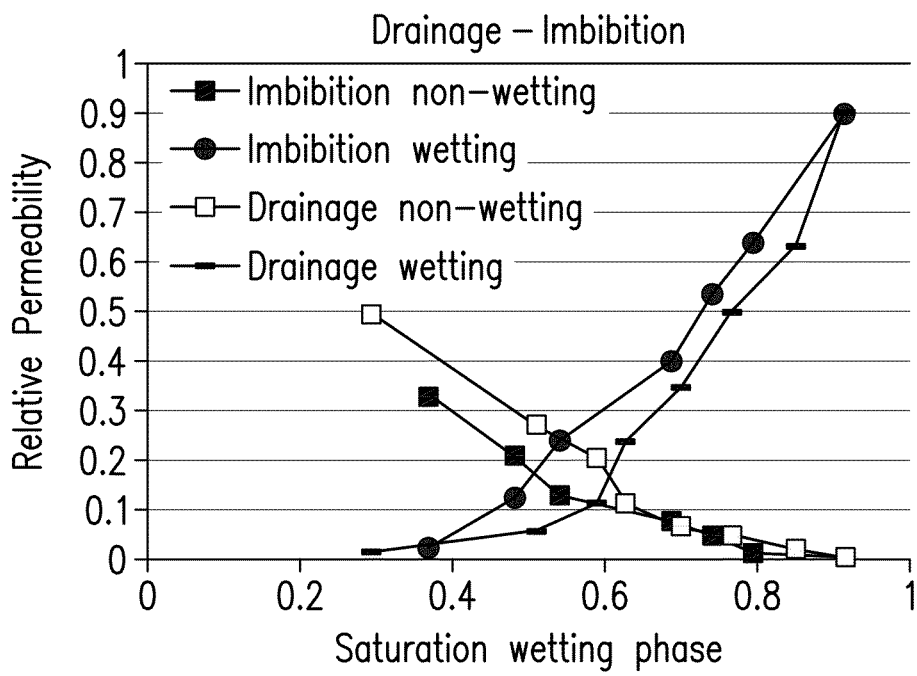
FIG. 1 shows a representative plot of a hysteresis effect in relative permeability under imbibition and drainage.
Figure 2:
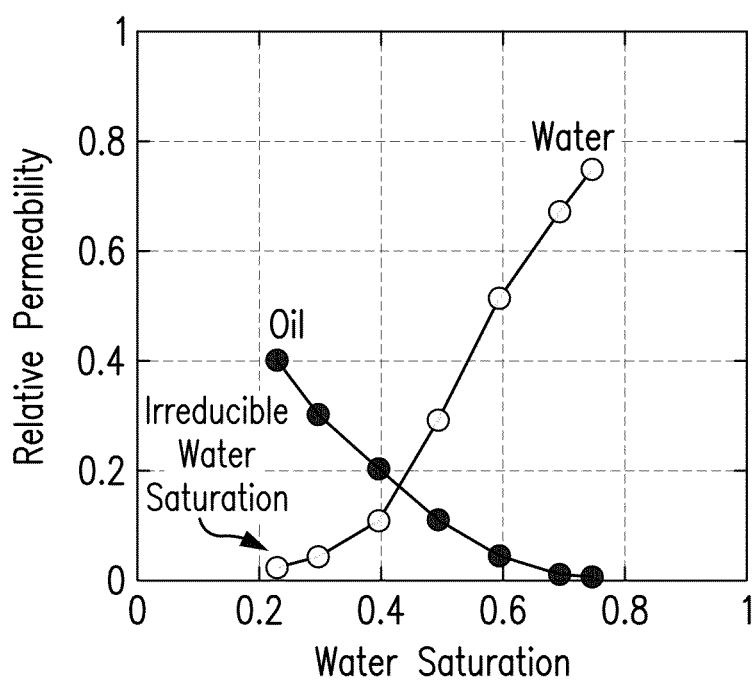
FIG. 2 is a representative plot of relative permeability for wetting and non-wetting fluids at saturation levels ranging from 0 to 1.

After all combinations of fractional wetting and non-wetting flows have been processed and flow rates, pressures and saturations have been calculated, imbibition and drainage relative permeabilities can be calculated for the water saturations corresponding to each pair of fractional flows (33). The relative permeabilities and saturations may be plotted (34) as shown in FIG. 1.

Figure 9:
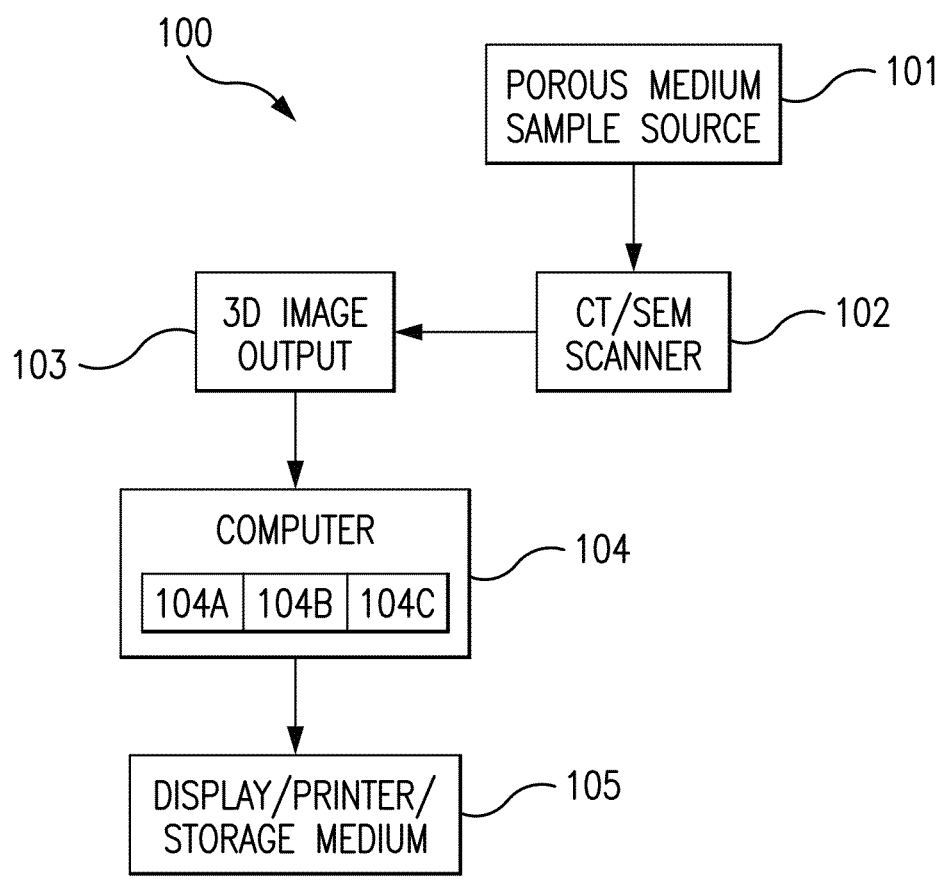
FIG. 9 shows a system which integrates three-dimensional (3D) scan imaging analysis of a porous medium with a computational fluid dynamics (CFD) method applied to a 3D digital representation of the porous medium, according to an example of the present application.

Referring to FIG. 9, a system 100 is shown which can be adapted for performing the present methods. As shown in this example, three dimensional (3D) images of the porous medium samples obtained from source 101 are generated by the scanner 102. The scanner can comprise, for example, a computer tomographic (CT) scanner, a scanning electron microscope (SEM), a focused ion beam scanning electron microscope (FIB-SEM), or similar device capable of producing a three dimensional digital image of a porous medium. The 3D image output 103 of the scanner can be transferred to a computer 104 having program instructions for carrying out the 3D image analysis, and the indicated CFD data and simulation analysis, to generate sample modeling output/results which can transmitted to one or more devices 105, such as a display, a printer, data storage medium, or combinations of these. The computer programs used for 3D image analysis and the CFD computations and simulation modeling can be stored, as a program product, on at least one computer usable storage medium 104B (e.g. a hard disk, a flash memory device, a compact disc, a magnetic tape/disk, or other media) associated with at least one processor 104A (e.g., a CPU) which is adapted to run the programs, or may be stored on an external computer usable storage medium (not shown) which is accessible to the computer processor. Computer 104 can include at least one memory unit 104C for storage of the programs, input data and output data, and other program results, or combinations of these. For output display, device 105 can be, for example, a display monitor, CRT, or other visual means of display (not shown). The computer 104 may include one or more system computers, which may be implemented as a single personal computer or as a network of computers. However, those skilled in the art will appreciate that implementations of various techniques described herein may be practiced in a variety of computer system configurations, including hypertext transfer protocol (HTTP) servers, hand-held devices, multiprocessor systems, microprocessor-based or programmable consumer electronics, network PCs, minicomputers, mainframe computers, and the like. The units of system 100 including scanner 102, computer 104, and output display and/or external data storage 105, can be connected to each other for communications (e.g., data transfer, etc.), via any of hardwire, radio frequency communications, telecommunications, internet connection, or other communication means.

The present invention includes the following aspects/embodiments/features in any order and/or in any combination:

1. The present invention relates to a method for simulating fractional flow of wetting fluids and non-wetting fluids through porous medium comprising the steps of:
   a) creating a three dimensional digital representation of a porous medium (Sample) containing a total volume of fluids comprising wetting fluids and non-wetting fluids,
   b) defining a first fraction of the total volume of fluids that comprises the wetting fluids and a second fraction of the total volume of fluids that comprises the non-wetting fluids,
   c) defining a value for a flow rate of the total volume of fluids flowing through the Sample,
   d) assessing properties of the wetting fluids and the non-wetting fluids,
   e) defining initial conditions for saturation of the wetting fluids (Sw), saturation of the non-wetting fluids (Sn), inlet pressure of the wetting fluids (Pw) and inlet pressure of the non-wetting fluids (Pn),
   f) setting conditions at the inlet face of the sample wherein non-wetting fluids and wetting fluids enter the pores of the Sample in separate and distinct areas, and
   g) calculating pressures, saturation, and velocity vectors internal to the Sample,
   h) calculating flow rates of the non-wetting fluids (Qn) through the Sample, flow rates of the wetting fluids (Qw) through the Sample, and pressure at the outlet of the Sample,
   i) repeating steps a) through h) for a predefined number of time increments, t, and
   j) periodically adjusting the inlet pressures Pn and Pw using a feedback control algorithm wherein quasi-steady state values for Qn and Qw are achieved.

2. The method of any preceding or following embodiment/feature/aspect, wherein the porous medium is rock, soil, zeolite, biological tissue, wood, cork, cement, ceramic, sand, clay, inorganic compound, organic compound, or metal.

3. The method of any preceding or following embodiment/feature/aspect, wherein the Sample comprises multiple, ordered planes of voxels, wherein each of the voxels represents a pore (pore voxel) or solid (grain voxel).

4. The method of any preceding or following embodiment/feature/aspect, wherein the properties of the wetting fluids comprise viscosity, contact angle, interfacial tension, other physical or chemical properties or any combinations thereof 5. The method of any preceding or following embodiment/feature/aspect, wherein the properties of the non-wetting fluids comprise viscosity, contact angle, interfacial tension, other physical or chemical properties or any combinations thereof 6. The method of any preceding or following embodiment/feature/aspect, wherein the Sample comprises (a) an inlet face and an outlet face wherein the inlet face and outlet face are parallel to each other, and (b) three or more surfaces orthogonal to the inlet face and the outlet face, wherein the three or more orthogonal surfaces are impervious to flow of the wetting fluids and the non-wetting fluids.

7. The method of any preceding or following embodiment/feature/aspect, wherein the inlet face further comprises a buffer zone parallel to the inlet face comprising at least one voxel plane.

8. The method of any preceding or following embodiment/feature/aspect, wherein an interfacial tension between the wetting fluid and non-wetting fluid is set to zero for all calculations within the buffer zone.

9. The method of any preceding or following embodiment/feature/aspect, wherein the interfacial tension between the wetting fluid and non-wetting fluid is set to zero and the viscosities of the wetting fluid and non-wetting fluid are increased by a factor of at least about 10 times for all calculations within the buffer zone.

10. The method of any preceding or following embodiment/feature/aspect, wherein the non-wetting fluids and the wetting fluids enter the Sample through pores on the inlet face of the Sample.
11. The method of any preceding or following embodiment/feature/aspect, wherein the pores on the inlet face comprise separate and distinct areas formed by allocating pore voxels immediately adjacent to a grain voxel for the flow of the wetting fluids (Aw) and remaining pore voxels are allocated for the flow of the non-wetting fluids (An).
12. The method of any preceding or following embodiment/feature/aspect, wherein the Aw is increased by further allocating pore voxels adjacent to Aw for the flow of the wetting fluids (Aw) and the remaining pore voxels are allocated for the flow of the non-wetting fluids (An).
13. The method of any preceding or following embodiment/feature/aspect, wherein (sum of voxels in An)/((sum of voxels in An)+(sum of voxels in Aw)) is approximately 0.5 or less.
14. The method of any preceding or following embodiment/feature/aspect, wherein the calculating comprises computational fluid dynamics.
15. The method of any preceding or following embodiment/feature/aspect, wherein the computational fluids dynamics comprises the lattice Boltzmann method.
16. The method of any preceding or following embodiment/feature/aspect, wherein the time increment, t, may be seconds, milli-seconds or other time unit.
17. The method of any preceding or following embodiment/feature/aspect, wherein the number of time increments is 10,000 or more.
18. The method of any preceding or following embodiment/feature/aspect, wherein the feedback control algorithm comprises a separate feedback control algorithm to set the inlet pressure for the wetting fluid and a separate feedback control algorithm to set the inlet pressure for the non-wetting fluid, wherein the inlet pressure for the wetting fluid and the inlet pressure for the non-wetting fluid are set independently.
19. The method of any preceding or following embodiment/feature/aspect, wherein the feedback control algorithm comprises one feedback control algorithm to set the inlet pressure for both the wetting and the non-wetting fluid, wherein the inlet pressure for the wetting fluid and the inlet pressure for the non-wetting fluid are equal.
20. The method of any preceding or following embodiment/feature/aspect, wherein the feedback control algorithm comprises a proportional-integral-derivative control loop, an adaptive control, a hierarchical control, an intelligent control, an optimal control, a robust control, a neural network control, a fuzzy logic control, or a stochastic control.
21. The method of any preceding or following embodiment/feature/aspect, wherein the feedback control algorithm is a negative feedback control algorithm.
22. The method of any preceding or following embodiment/feature/aspect, wherein the feedback control algorithm comprises a proportional-integral-derivative (PID) control loop.
23. The method of any preceding or following embodiment/feature/aspect, wherein the PID control loop comprises an input error Ew and outputs a new inlet pressure, Pw, wherein $Pw=Pi+Pi*\pi w$ Pi=the initial pressure set at the beginning of the simulation $$\pi w = f(Ew) \text{ such as } K_P*Ew + K_I \int Ewdt + K_D \frac{dEw}{dt}$$

$K_p$=proportional control constant,
$K_I$=integral control constant,
$K_D$=derivative control constant, $Ew=QwT-QW$, and $QwT=QT*Fw$, QT=the target total flow rate through the Sample,
Fw=the fraction of wetting fluid that enters the inlet face of the Sample,
QW=an average of values of Qwt, and
Qwt=the calculated flow rate of wetting fluid and time interval, t.

24. The method of any preceding or following embodiment/feature/aspect, wherein QW comprises an arithmetic weighted average, a geometric weighted average, a harmonic weighted average, a simple rolling average, an exponentially weighted moving average or other method of averaging a series of numbers.
25. The method of any preceding or following embodiment/feature/aspect, wherein the PID control loop comprises an input error En and outputs a new inlet pressure, Pn, wherein $Pn=Pi+Pi*\pi n$ Pi=the initial pressure set at the beginning of the simulation $$\pi n = f(En) \text{ such as } K_P*En + K_I \int Endt + K_D \frac{dEn}{dt}$$

$K_p$=proportional control constant,
$K_I$=integral control constant,
$K_D$=derivative control constant, $En=QnT-QN$, and $QnT=QT*Fn$, QT=the target total flow rate through the Sample,
Fn=the fraction of non-wetting fluid that enters the inlet face of the Sample,
QN=an average of values of Qnt, and
Qnt=the calculated flow rate of non-wetting fluid and time interval, t.

26. The method of any preceding or following embodiment/feature/aspect, wherein QN comprises an arithmetic weighted average, a geometric weighted average, a harmonic weighted average, a simple rolling average, an exponentially weighted moving average or other method of averaging a series of numbers.
27. The method of any preceding or following embodiment/feature/aspect, wherein the PID control loop comprises an input error Ec and outputs a new inlet pressure, Pc, wherein $Pc=Pi+Pi*\pi c$ Pi=the initial pressure set at the beginning of the simulation $$\pi c = f(Ec) \text{ such as } K_P*Ec + K_I \int Ecdt + K_D \frac{dEc}{dt}$$

$K_P$=proportional control constant,
$K_I$=integral control constant,
$K_D$=derivative control constant, $$Ec=QT-QC, \text{ and}$$

QT=the target total flow rate through the Sample,
QC=an average of values of Qwt+Qnt,
Qnt=the calculated flow rate of non-wetting fluid and time interval, t, and
Qwt=the calculated flow rate of wetting fluid and time interval, t.

28. The method of any preceding or following embodiment/feature/aspect, wherein QT comprises an arithmetic weighted average, a geometric weighted average, a harmonic weighted average, a simple rolling average, an exponentially weighted moving average or other method of averaging a series of numbers.

29. The method of any preceding or following embodiment/feature/aspect, wherein the periodically adjusting inlet pressures occurs about once every 10 time increments or higher.

30. The method of any preceding or following embodiment/feature/aspect, wherein the number of time increments of subsequent periodical adjustments of inlet pressure are different.

31. The method of any preceding or following embodiment/feature/aspect, wherein the periodically adjusting inlet pressures occurs more often in the first half of the total time of the simulation than in the second half of the simulation.

32. The method of any preceding or following embodiment/feature/aspect, wherein the periodically adjusting inlet pressures in the first half of the total time of simulation occurs at least 10 times more than in the second half.

33. The method of any preceding or following embodiment/feature/aspect, wherein quasi-steady state is where the calculated values of Qn, Qw, Pn, Pw and/or saturation vary no more than a pre-determined value.

34. The method of any preceding or following embodiment/feature/aspect, wherein the predefined number of time increments, t, are set sufficiently large to achieve quasi-steady state.

35. A method for calculating relative permeability of wetting and non-wetting fluids flowing through a porous medium comprising
   a) defining a series of pairs of non-wetting fluids and wetting fluids, each pair to be forced through the Sample,
   b) setting an initial Sample saturation,
   c) forcing each pair of non-wetting and wetting fluids through the Sample,
   d) recording calculated values of QN, QW and wetting fluid saturation, Sw for each pair of wetting and non-wetting fluids,
   e) calculating values of relative permeability of the wetting fluid, kw; calculating values of the relative permeability of the non-wetting fluid, kn; and calculating values of the water saturation, Sw, and
   f) generating a plot of values of kw and kn versus Sw.

36. The method of any preceding or following embodiment/feature/aspect, wherein the porous medium is rock, soil, zeolite, biological tissue, wood, cork, cement, ceramic, sand, clay, rock, inorganic compound, organic compound, or metal.

37. The method of any preceding or following embodiment/feature/aspect, wherein a pair of non-wetting and wetting fluid comprise a fractional composition of the non-wetting fluid and a fractional value of the wetting fluid (Fn, Fw).

38. The method of any preceding or following embodiment/feature/aspect, wherein the pair of non-wetting and wetting fluid comprise a plurality of pairs of (Fn, Fw), wherein any combination of Fn and Fw has a sum that is equal to 1.

39. The method of any preceding or following embodiment/feature/aspect, wherein the pair of non-wetting and wetting fluid comprise a plurality of pairs of (Fn', Fw'), wherein Fn' is calculated as the value of (Fn×R) and Fw' is calculated as the value of (1−(Fn×R)), wherein R is the ratio of viscosities of the low viscosity phase to the high viscosity phase of the wetting and non-wetting fluids, and any combination of Fn' and Fw' has a sum that is equal to 1.

40. The method of any preceding or following embodiment/feature/aspect, wherein the pairs of non-wetting and wetting fluid comprise an ordered series of values in which Fn decreases in steps to zero and then increases to 1.0.

41. The method of any preceding or following embodiment/feature/aspect, wherein the initial Sample saturation is a total wetting fluid saturation, Sw,=1.0, and a total non-wetting fluid saturation, Sn,=1.0.

42. The method of any preceding or following embodiment/feature/aspect, wherein the initial Sample saturation is the ending saturation conditions from a previous simulation.

43. The method of any preceding or following embodiment/feature/aspect, wherein the fractional area of the pores on the inlet face allocated for injection of non-wetting fluid, An, is decreased when Fn is less than about 0.2.

44. The method of any preceding or following embodiment/feature/aspect, wherein An is reduced to about 0.4 or less.

45. A system computing fractional multi-phase, multi-component flow through a porous medium comprising:
   a) a scanner capable of producing a three dimensional digital image of a porous medium,
   b) a computer comprising at least one processor operable for executing a computer program capable of classifying elements in the three dimensional digital image as solid (grain) and pore (void),
   c) a computer (same or different from b)) comprising at least one processor operable for executing a computer program capable of performing computations, wherein said computations comprise (i) creating a three dimensional digital representation of a porous medium (Sample) containing a total volume of fluids comprising wetting fluids and non-wetting fluids, (ii) defining a first fraction of the total volume of fluids that comprises the wetting fluids and defining a second fraction of the total volume of fluids that comprises the non-wetting fluids, (iii) defining a value for a flow rate of the total volume of fluids flowing through the Sample, (iv) assessing properties of the wetting fluids and the non-wetting fluids, (v) defining initial conditions for saturation of the wetting fluids (Sw), saturation of the non-wetting fluids (Sn), inlet pressure of the wetting fluids (Pw) and inlet pressure of the non-wetting fluids (Pn), (vi) setting conditions at the inlet face of the sample wherein non-wetting fluids and wetting fluids enter the pores of the Sample in separate and distinct areas, and (vii) calculating pressures, saturation, and velocity vectors internal to a Sample of the porous medium, (viii) calculating flow rates of the non-wetting fluids (Qn) through the Sample, flow rates of the wetting fluids (Qw) through the Sample, and pressure at the outlet of the Sample, (ix) repeating steps (i) through (viii) for a predefined number of time increments, t, and (x) periodically adjusting the inlet pressures Pn and Pw using a feedback control algorithm wherein quasi-steady state values for Qn and Qw are achieved, and d) at least one device to display, print, or store results of the computations.
46. The system of any preceding or following embodiment/feature/aspect, wherein the scanner comprises a computer tomographic (CT) scanner, a scanning electron microscope (SEM), a focused ion bean scanning electron microscope (FIB-SEM), or similar device capable of producing a three dimensional digital image of a porous medium.
47. The system of any preceding or following embodiment/feature/aspect, wherein the device comprises a memory device for retrievably storing the results of said computations.
48. A computer program product on a computer readable medium that, when performed on a controller in a computerized device provides a method for performing the computations of any preceding or following embodiment/feature/aspect. This computer program can be on a non-transitory storage medium and/or the computer readable storage medium can exclude signals.

The present invention can include any combination of these various features or embodiments above and/or below as set forth in sentences and/or paragraphs. Any combination of disclosed features herein is considered part of the present invention and no limitation is intended with respect to combinable features.

The present invention will be further clarified by the following examples which are intended to be only exemplary in nature.

EXAMPLES

Example 1

A sample of a carbonate rock was selected for analysis using a representative method of the present invention. The sample plug was weighed (125.299 g), physically measured for its diameter and length, and photographed. The plug was marked for orientation and placed in oven to dry and weighed again (124.447 g).

The plug was imaged on a MicroXCT-200 manufactured by Xradia at a resolution of 0.5x, at approximately 40 microns (pm) per voxel. The plug was scanned with the Ceretom Dual Energy X-Ray CT Scanner manufactured by Neurologica to determine bulk density and atomic number. A sub-sampling location was selected that showed typical atomic number. Areas with high atomic number were avoided.

Figure 10:
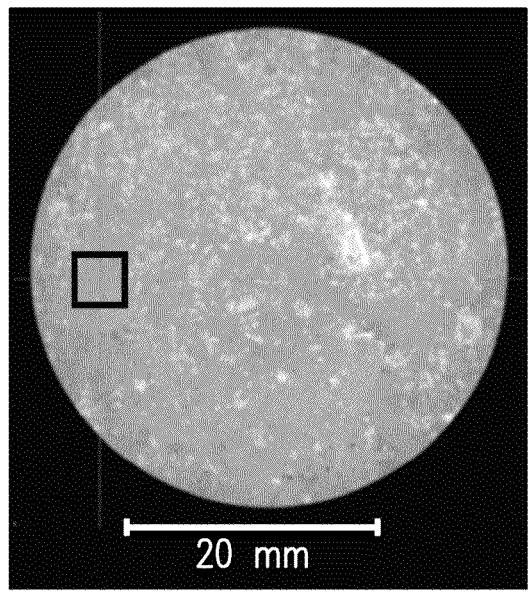
FIG. 10 shows a representative photograph of a carbonate sample which includes a 4 mm diameter pillar marked by a rectangle which was milled out of the sample and imaged on a CT scanner, according to an example of the present application.
Figure 11:
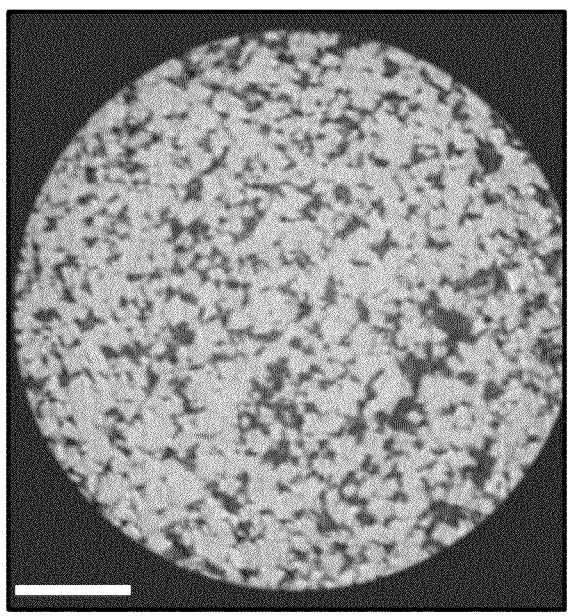
FIG. 11 shows a representative scanned image with the CT scanner of the selected area of the carbonate sample indicated in FIG. 10, according to an example of the present application.

A laser was used to mill out a 4 mm diameter pillar from the carbonate sample (see the square region indicated in FIG. 10). The square region in FIG. 10 is the area of the carbonate sample selected for further analysis. The selected sub-sample was imaged on the MicroXCT-200 scanner at a resolution of 40x, approximately 500 nanometers per voxel. The resulting scanned image of the selected sub-sample is shown in FIG. 11.

The image was reconstructed and cropped to a 500×500×500 voxel cube for segmentation. The image was segmented in a manner indicated herein and absolute permeability, formation factor and elasticity were estimated using methods available in the literature. Permeability in the z direction was 22 mD and the porosity was 0.21.

The segmented image was cropped to a 200×200×260 voxel cube, keeping approximately the same absolute permeability and porosity in the direction of flow. In this way, the segmented image used for relative permeability estimation using a method of the present invention has dimension of 200×200 lattice points in the X and Y direction and 260 lattice points in the direction parallel to the applied pressure gradient. The two fluids used in this example are brine and oil with the following properties:

dynamic viscosity Brine at 21° C. and standard pressure 1.664 cp, and dynamic viscosity Oil at 21° C. and standard pressure 7.71 cp.

The following initial conditions were set for the simulation:

flow rate (Darcy) at steady state is 255 ft/day, interfacial tension between the two fluids is 35 dyn/cm, the contact angle is 45 degrees, so that the water is considered the wetting fluid, and each time step in the simulation corresponds to 0.1 micro second.

At t=0, the segmented image is filled with 100% oil and the water is injected at different flow rates inside the segmented image. At t=0, the inlet area is 100% assigned to the wetting phase, water in this case, so that a primary water flooding is performed (100% water injection).

After the initial flooding, the inlet plane was divided into two areas (the area close to the solid for injection of the wetting fluid and the central pore area for the non-wetting fluid) with 67% of the area allocated for the wetting fluid. This wetting fluid area, 67%, was maintained for fractional oil flows of 30%, 50%, 70%, and 80% by volume. For higher fractional oil flows (90%, 93%, 96%), the wetting fluid area at the inlet was increased to 82% of the total pore inlet area. 1.5 million time steps were used for the initial flooding step. 1 million time steps were used for subsequent water injections.

The first correction with the control feedback loop was performed after 50 time steps. The second correction with the control feedback loop was performed after 5,000 time steps. The control feedback loop was performed every 1,000 time steps from 5,001 to 150,000 time steps, and every 10,000 time steps from 150,001 to either 1.5 million time steps (for the first flooding) or to 1 million time steps for the following fractional flow injections. Every time that the fractional flow was changed at the inlet, the frequency of the feedback controller action was increased to every 1,000 time steps until 150,000 subsequent time steps are completed.

The constant C in the initial pressure was set to 25, having an initial pressure of 1.8 K Pa. The proportional, integral and derivative constants in the PID controller were set to 10,000, 5,000 (1/timesteps) and 1,000 (timesteps) respectively. The width of the exponential time average window was such that 33% of the new value and 66% of the previous values were summed together. The surface tension in the buffer inlet region was set to zero. The length of the buffer was set to 15 lattice units.

Figure 12:
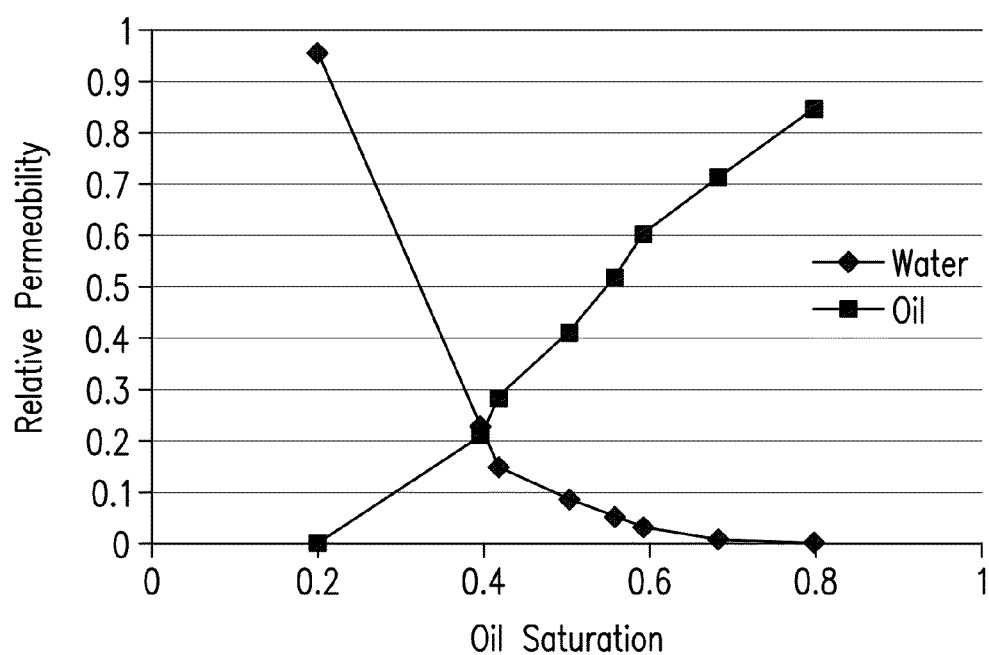
FIG. 12 shows a representative plot of relative permeability and water saturation values estimated using a method according to an example of the present application.

The relative permeability and water saturation values estimated for these criteria using the method of the present invention are shown in FIG. 12.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method for simulating fractional flow of wetting fluids and non-wetting fluids through porous medium comprising the steps of:
   a) creating a three dimensional digital representation of a physical sample of a porous medium (Sample) containing a total volume of fluids comprising wetting fluids and non-wetting fluids, wherein the creating comprises scanning the Sample with a device producing a three-dimensional (3D) digital representation of porous structure of the Sample,
   b) defining a first fraction of the total volume of fluids that comprises the wetting fluids and a second fraction of the total volume of fluids that comprises the non-wetting fluids,
   c) defining a value for a flow rate of the total volume of fluids flowing through the Sample,
   d) assessing properties of the wetting fluids and the non-wetting fluids,
   e) defining initial conditions for saturation of the wetting fluids (Sw), saturation of the non-wetting fluids (Sn), inlet pressure of the wetting fluids (Pw) and inlet pressure of the non-wetting fluids (Pn),
   f) setting conditions at the inlet face of the Sample wherein non-wetting fluids and wetting fluids enter the pores of the Sample in separate and distinct areas, and
   g) calculating pressures, saturation, and velocity vectors internal to the Sample,
   h) calculating flow rates of the non-wetting fluids (Qn) through the Sample, flow rates of the wetting fluids (Qw) through the Sample, and pressure at the outlet of the Sample,
   i) repeating steps a) through h) for a predefined number of time increments, t, and
   j) periodically adjusting the inlet pressures Pn and Pw using a feedback control algorithm wherein quasi-steady state values for Qn and Qw are achieved.

2. The method of claim 1, wherein the porous medium is rock, soil, zeolite, biological tissue, wood, cork, cement, ceramic, sand, clay, inorganic compound, organic compound, or metal.

3. The method of claim 1, wherein the Sample comprises multiple, ordered planes of voxels, wherein each of the voxels represents a pore (pore voxel) or solid (grain voxel).

4. The method of claim 1, wherein the properties of the wetting fluids comprise viscosity, contact angle, interfacial tension, other physical or chemical properties or any combinations thereof.

5. The method of claim 1, wherein the properties of the non-wetting fluids comprise viscosity, contact angle, interfacial tension, other physical or chemical properties or any combinations thereof.

6. The method of claim 1, wherein the Sample comprises (a) an inlet face and an outlet face wherein the inlet face and outlet face are parallel to each other, and (b) three or more surfaces orthogonal to the inlet face and the outlet face, wherein the three or more orthogonal surfaces are impervious to flow of the wetting fluids and the non-wetting fluids.

7. The method of claim 6, wherein the inlet face further comprises a buffer zone parallel to the inlet face comprising at least one voxel plane.

8. The method of claim 7, wherein an interfacial tension between the wetting fluid and non-wetting fluid is set to zero for all calculations within the buffer zone.

9. The method of claim 8, wherein the interfacial tension between the wetting fluid and non-wetting fluid is set to zero and the viscosities of the wetting fluid and non-wetting fluid are increased by a factor of at least about 10 times for all calculations within the buffer zone.

10. The method of claim 1, wherein the non-wetting fluids and the wetting fluids enter the Sample through pores on the inlet face of the Sample.

11. The method of claim 10, wherein the pores on the inlet face comprise separate and distinct areas formed by allocating pore voxels immediately adjacent to a grain voxel for the flow of the wetting fluids (Aw) and remaining pore voxels are allocated for the flow of the non-wetting fluids (An).

12. The method of claim 11, wherein the Aw is increased by further allocating pore voxels adjacent to Aw for the flow of the wetting fluids (Aw) and the remaining pore voxels are allocated for the flow of the non-wetting fluids (An).

13. The method of claim 11, wherein (sum of voxels in An)/((sum of voxels in An)+(sum of voxels in Aw)) is approximately 0.5 or less.

14. The method of claim 1, wherein the calculating comprises computational fluid dynamics.

15. The method of claim 14, wherein the computational fluids dynamics comprises the lattice Boltzmann method.

16. The method of claim 1, wherein the time increment, t, is seconds, milli-seconds or other time unit.

17. The method of claim 1, wherein the number of time increments is 10,000 or more.

18. The method of claim 1, wherein the feedback control algorithm comprises a separate feedback control algorithm to set the inlet pressure for the wetting fluid and a separate feedback control algorithm to set the inlet pressure for the non-wetting fluid, wherein the inlet pressure for the wetting fluid and the inlet pressure for the non-wetting fluid are set independently.

19. The method of claim 1, wherein the feedback control algorithm comprises one feedback control algorithm to set the inlet pressure for both the wetting and the non-wetting fluid, wherein the inlet pressure for the wetting fluid and the inlet pressure for the non-wetting fluid are equal.

20. The method of claim 1, wherein the feedback control algorithm comprises a proportional-integral-derivative control loop, an adaptive control, a hierarchical control, an intelligent control, an optimal control, a robust control, a neural network control, a fuzzy logic control, or a stochastic control.

21. The method of claim 1, wherein the feedback control algorithm is a negative feedback control algorithm.

22. The method of claim 1, wherein the feedback control algorithm comprises a proportional-integral-derivative (PID) control loop.

23. The method of claim 22, wherein the PID control loop comprises an input error Ew and outputs a new inlet pressure, Pw, wherein $$Pw = Pi + Pi * \pi w$$

Pi=the initial pressure set at the beginning of the simulation $$\pi w = f(Ew) \text{ comprising } K_P * Ew + K_I \int Ew dt + K_D \frac{dEw}{dt}$$

$K_P$=proportional control constant,
$K_I$=integral control constant,
$K_D$=derivative control constant, $Ew=QwT-QW$, and $QwT=QT*Fw$, QT=the target total flow rate through the Sample,
Fw=the fraction of wetting fluid that enters the inlet face of the Sample,
QW=an average of values of Qwt, and
Qwt=the calculated flow rate of wetting fluid and time interval, t.

24. The method of claim 23, wherein QW comprises an arithmetic weighted average, a geometric weighted average, a harmonic weighted average, a simple rolling average, an exponentially weighted moving average or other method of averaging a series of numbers.

25. The method of claim 22, wherein the PID control loop comprises an input error En and outputs a new inlet pressure, Pn, wherein $Pn=Pi+Pi*\pi n$ Pi=the initial pressure set at the beginning of the simulation $$\pi n = f(En) \text{ comprising } K_P * En + K_I \int En dt + K_D \frac{dEn}{dt}$$

$K_P$=proportional control constant,
$K_I$=integral control constant,
$K_D$=derivative control constant, $En=QnT-QN$, and $QnT=QT*Fn$, QT=the target total flow rate through the Sample,
Fn=the fraction of non-wetting fluid that enters the inlet face of the Sample,
QN=an average of values of Qnt, and
Qnt=the calculated flow rate of non-wetting fluid and time interval, t.

26. The method of claim 25, wherein QN comprises an arithmetic weighted average, a geometric weighted average, a harmonic weighted average, a simple rolling average, an exponentially weighted moving average or other method of averaging a series of numbers.

27. The method of claim 22, wherein the PID control loop comprises an input error Ec and outputs a new inlet pressure, Pc, wherein $Pc=Pi+Pi*\pi c$ Pi=the initial pressure set at the beginning of the simulation $$\pi c = f(Ec) \text{ comprising } K_P * Ec + K_I \int Ec dt + K_D \frac{dEc}{dt}$$

$K_P$=proportional control constant,
$K_I$=integral control constant,
$K_D$=derivative control constant, $Ec=QT-QC$, and QT=the target total flow rate through the Sample,
QC=an average of values of Qwt+Qnt,
Qnt=the calculated flow rate of non-wetting fluid and time interval, t, and
Qwt=the calculated flow rate of wetting fluid and time interval, t.

28. The method of claim 27, wherein QT comprises an arithmetic weighted average, a geometric weighted average, a harmonic weighted average, a simple rolling average, an exponentially weighted moving average or other method of averaging a series of numbers.

29. The method of claim 1, wherein the periodically adjusting inlet pressures occurs about once every 10 time increments or higher.

30. The method of claim 29, wherein the number of time increments of subsequent periodical adjustments of inlet pressure are different.

31. The method of claim 1, wherein the periodically adjusting inlet pressures occurs more often in the first half of the total time of the simulation than in the second half of the simulation.

32. The method of claim 31, wherein the periodically adjusting inlet pressures in the first half of the total time of simulation occurs at least 10 times more than in the second half.

33. The method of claim 1, wherein quasi-steady state is where the calculated values of Qn, Qw, Pn, Pw and/or saturation vary no more than a pre-determined value.

34. The method of claim 1, wherein the predefined number of time increments, t, are set sufficiently large to achieve quasi-steady state.

35. A method for calculating relative permeability of wetting and non-wetting fluids flowing through a porous medium comprising
a) defining a series of pairs of non-wetting fluids and wetting fluids, each pair to be forced through a three-dimensional (3D) digital representation of porous structure of a Sample of a porous medium, wherein the three-dimensional digital representation of porous structure of the Sample is created by scanning the Sample with a device that produces a three dimensional digital image of the porous medium,
b) setting an initial Sample saturation, and setting conditions at the inlet face of the Sample wherein non-wetting fluids and wetting fluids enter the pores of the Sample in separate and distinct areas,
c) forcing each pair of non-wetting and wetting fluids through the Sample,
d) recording calculated values of QN, QW and wetting fluid saturation, Sw for each pair of wetting and non-wetting fluids, wherein QN=an average of values of Qnt, and Qnt=the calculated flow rate of non-wetting fluid and time interval, t, and QW=an average of values of Qwt, and Qwt=the calculated flow rate of wetting fluid and time interval, t,
e) calculating values of relative permeability of the wetting fluid, kw; calculating values of the relative permeability of the non-wetting fluid, kn; and calculating values of the water saturation, Sw, and
f) generating a plot of values of kw and kn versus Sw.

36. The method of claim 35, wherein the porous medium is rock, soil, zeolite, biological tissue, wood, cork, cement, ceramic, sand, clay, rock, inorganic compound, organic compound, or metal.

37. The method of claim 35, wherein a pair of non-wetting and wetting fluid comprise a fractional composition of the non-wetting fluid and a fractional value of the wetting fluid (Fn, Fw).

38. The method of claim 37, wherein the pair of non-wetting and wetting fluid comprise a plurality of pairs of (Fn, Fw) wherein any combination of Fn and Fw has a sum that is equal to 1.

39. The method of claim 37, wherein the pair of non-wetting and wetting fluid comprise a plurality of pairs of (Fn', Fw') wherein Fn' is calculated as the value of (Fn×R) and Fw' is calculated as the value of (1-(Fn×R)), wherein R is the ratio of viscosities of the low viscosity phase to the high viscosity phase of the wetting and non-wetting fluids, and any combination of Fn' and Fw' has a sum that is equal to 1.

40. The method of claim 37, wherein the pairs of non-wetting and wetting fluid comprise an ordered series of values in which Fn decreases in steps to zero and then increases to 1.0.

41. The method of claim 35, wherein the initial Sample saturation is a total wetting fluid saturation, Sw,=1.0, and a total non-wetting fluid saturation, Sn,=1.0.

42. The method of claim 35, wherein the initial Sample saturation is the ending saturation conditions from a previous simulation.

43. The method of claim 35, wherein the fractional area of the pores on the inlet face allocated for injection of non-wetting fluid, An, is decreased when Fn is less than about 0.2.

44. The method of claim 43, wherein An is reduced to about 0.4 or less.

45. A system computing fractional multi-phase, multi-component flow through a porous medium comprising:
   a) a scanner capable of producing a three dimensional digital image of a porous medium,
   b) a computer comprising at least one processor operable for executing a computer program capable of classifying elements in the three dimensional digital image as solid (grain) and pore (void),
   c) a computer (same or different from b)) comprising at least one processor operable for executing a computer program capable of performing computations, wherein said computations comprise (i) creating a three dimensional digital representation of a porous medium (Sample) containing a total volume of fluids comprising wetting fluids and non-wetting fluids, (ii) defining a first fraction of the total volume of fluids that comprises the wetting fluids and defining a second fraction of the total volume of fluids that comprises the non-wetting fluids, (iii) defining a value for a flow rate of the total volume of fluids flowing through the Sample, (iv) assessing properties of the wetting fluids and the non-wetting fluids, (v) defining initial conditions for saturation of the wetting fluids (Sw), saturation of the non-wetting fluids (Sn), inlet pressure of the wetting fluids (Pw) and inlet pressure of the non-wetting fluids (Pn), (vi) setting conditions at the inlet face of the sample wherein non-wetting fluids and wetting fluids enter the pores of the Sample in separate and distinct areas, and (vii) calculating pressures, saturation, and velocity vectors internal to a Sample of the porous medium, (viii) calculating flow rates of the non-wetting fluids (Qn) through the Sample, flow rates of the wetting fluids (Qw) through the Sample, and pressure at the outlet of the Sample, (ix) repeating steps (i) through (viii) for a predefined number of time increments, t, and (x) periodically adjusting the inlet pressures Pn and Pw using a feedback control algorithm wherein quasi-steady state values for Qn and Qw are achieved, and
   d) at least one device to display, print, or store results of the computations.

46. The system of claim 45, wherein the scanner comprises a computer tomographic (CT) scanner, a scanning electron microscope (SEM), a focused ion bean scanning electron microscope (FIB-SEM), or similar device capable of producing a three dimensional digital image of a porous medium.

47. The system of claim 45, wherein the device comprises a memory device for retrievably storing the results of said computations.

48. A non-transitory computer-readable storage medium that, when performed on a controller in a computerized device provides a method for performing the computations of claim 45.

* * * * *